United States Patent
Sheng et al.

(10) Patent No.: US 11,639,341 B2
(45) Date of Patent: May 2, 2023

(54) CRYSTAL FORM OF TIPIFARNIB AND METHOD OF TREATMENT THEREOF

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN); Yanli Dai, Zhejiang (CN)

(73) Assignee: Hangzhou SoliPharma Co., Ltd., Hangzhou (CN)

( * ) Notice: Subject to any disclaimer, the term of this patent is extended or adjusted under 35 U.S.C. 154(b) by 292 days.

(21) Appl. No.: 17/133,508

(22) Filed: Dec. 23, 2020

(65) Prior Publication Data

US 2021/0214335 A1    Jul. 15, 2021

Related U.S. Application Data

(62) Division of application No. 16/467,515, filed as application No. PCT/CN2016/108970 on Dec. 8, 2016, now Pat. No. 10,954,210.

(51) Int. Cl.
*C07D 401/06* (2006.01)

(52) U.S. Cl.
CPC ........ *C07D 401/06* (2013.01); *C07B 2200/13* (2013.01)

(58) Field of Classification Search
CPC combination set(s) only.
See application file for complete search history.

(56) References Cited

U.S. PATENT DOCUMENTS

| 6,169,096 | B1 | 1/2001 | Venet et al. |
| 6,420,387 | B1 | 7/2002 | Venet et al. |
| 6,844,439 | B2 | 1/2005 | Filliers et al. |
| 7,456,287 | B2 | 11/2008 | Filliers et al. |
| 10,954,210 | B2 | 3/2021 | Sheng et al. |
| 2009/0042935 | A1 | 2/2009 | De Porre et al. |
| 2014/0356322 | A1 | 12/2014 | Crews et al. |

FOREIGN PATENT DOCUMENTS

| CN | 1203598 A | 12/1998 |
| CN | 1101392 C | 2/2003 |
| CN | 1496363 A | 5/2004 |
| CN | 1246318 C | 3/2006 |
| CN | 100567292 C | 12/2009 |
| CN | 104736569 A | 6/2015 |
| CN | 105616361 A | 6/2016 |
| CN | 106176584 A | 12/2016 |
| WO | WO-2005105784 A1 | 11/2005 |
| WO | WO-2018103027 A1 | 6/2018 |

OTHER PUBLICATIONS

International Search Report and Written Opinion for Application No. PCT/CN2016/108970, dated Aug. 30, 2017, 19 pages, State Intellectual Property Office of the P. R. China, China (with English Translation).

*Primary Examiner* — Kathrien A Hartsfield

(74) *Attorney, Agent, or Firm* — Sterne, Kessler, Goldstein & Fox P.L.L.C.

(57) ABSTRACT

The present invention relates to novel crystal forms of tipifarnib. Compared with the prior art, the crystal forms of tipifarnib have advantages in crystallinity, hygroscopicity, morphology, form stability and chemical stability. The present invention also relates to the preparation methods of crystal forms of tipifarnib, pharmaceutical composition thereof and their use in preparation for treating and/or preventing abnormal cell growth diseases.

24 Claims, 8 Drawing Sheets

CRYSTAL FORM OF TIPIFARNIB AND METHOD OF TREATMENT THEREOF

CROSS-REFERENCE TO RELATED APPLICATIONS

This application is a divisional application of U.S. patent application Ser. No. 16/467,515 filed on Jun. 7, 2019, which is a U.S. national stage application of International Application No. PCT/CN2016/108970, filed on Dec. 8, 2016, each of which is herein incorporated by reference in its entirety.

FIELD OF THE INVENTION

The present invention relates to the technical field of crystallization in pharmaceutical chemistry. Specifically, the present invention relates to novel crystals, preparation methods and pharmaceutical compositions of tipifarnib.

BACKGROUND

Tipifarnib is a farnesyltransferase inhibitor that targets H-RAS or N-RAS mutant cells and has anti-proliferative effects. It is capable of blocking the farneylation modification of RAS protein, thereby interfering with RAS localization to the inner surface of the plasma membrane and subsequent activation of downstream signaling pathways. Tipifarnib shows effective anti-tumor activity.

Tipifarnib has the chemical name of (R)-6-(amino(4-chlorophenyl)(1-methyl-1H-imidazol-5-yl)methyl)-4-(3-chlorophenyl)-1-methyl-2(1H)-quinolinone. The chemical structure is shown in the following formula:

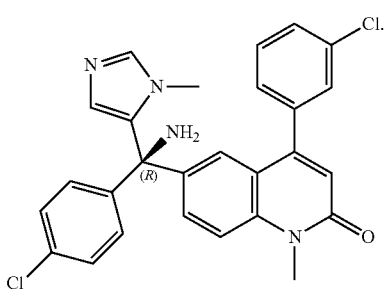

Patent document CN1101392C reported the preparation method of tipifarnib which was a racemic mixture and the patent did not disclose any characterization data. Patent document CN100567292C reported the preparation method of tipifarnib, which was a mixture with certain enantiomeric excesses and the patent only mentioned the melting point of the mixture. Patent document CN1246318C reported the preparation method of tipifarnib and the resolution and purification method of tipifarnib in enantiomers. The present inventors have found that tipifarnib prepared by the method described in patent document CN1246318C is crystalline (herein as "Form A"), but has the defects of low crystallinity and poor phase stability. Tipifarnib, reported in patent documents CN1101392C and CN100567292C are both mixtures and lack characteristic data that accurately describes their physical forms, therefore cannot be considered as sufficiently disclosed content.

In view of the disadvantages in the prior art, it is necessary to develop new solid forms of tipifarnib with more advantageous properties to meet the strict requirements of pharmaceutical preparations on the morphology, stability and other physicochemical properties of active substances.

SUMMARY OF THE INVENTION

According to the defects in the prior art, the objective of the present invention is to provide new crystalline forms of tipifarnib, preparation methods, pharmaceutical compositions and uses thereof. The crystalline forms are stable crystalline solids with one or more improved properties, especially in the aspects of crystallinity, hygroscopicity, morphology, processability of the formulation and solid-state form stability.

According to the objective of the invention, the first aspect of the invention is to provide a solid-state tipifarnib Form I (hereinafter referred to as "Form I") and its preparation method.

The present invention provides Form I with its structure shown in the formula (I) below:

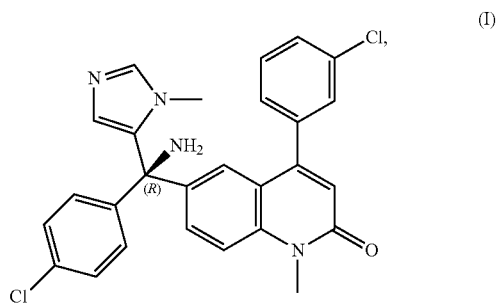

using Cu-Kα radiation, the X-ray powder diffraction pattern of Form I, expressed as 2θ angles, has the following characteristic peaks: 8.4°±0.2°, 11.9°±0.2°, 16.4°±0.2°, 17.0°±0.2°, 18.5°±0.2° and 21.7°±0.2°.

In a preferred embodiment of the present invention, the X-ray powder diffraction pattern of Form I, expressed as 2θ angles, has the following characteristic peaks: 8.4°±0.2°, 11.9°±0.2°, 15.3°±0.2°, 16.4°±0.2°, 17.0°±0.2°, 18.0°±0.2°, 18.5°±0.2°, 20.4°±0.2°, 21.3°±0.2°, 21.7°±0.2°, 24.8°±0.2° and 26.8°±0.2°.

In a further preferred embodiment of the present invention, the X-ray powder diffraction pattern of Form I, expressed as 2θ angles, has the following characteristic peaks and relative intensities:

| Diffraction angel 2θ | Relative intensity % |
|---|---|
| 8.4° ± 0.2° | 60.2 |
| 11.9° ± 0.2° | 34.6 |
| 12.7° ± 0.2° | 16.7 |
| 14.0° ± 0.2° | 9.3 |
| 15.3° ± 0.2° | 28.4 |
| 16.4° ± 0.2° | 82.7 |
| 17.0° ± 0.2° | 72.3 |
| 17.4° ± 0.2° | 32.2 |
| 18.0° ± 0.2° | 33.8 |
| 18.5° ± 0.2° | 100 |
| 19.9° ± 0.2° | 13.2 |
| 20.4° ± 0.2° | 55.2 |
| 20.8° ± 0.2° | 28.2 |
| 21.3° ± 0.2° | 61.5 |
| 21.7° ± 0.2° | 61.9 |
| 22.9° ± 0.2° | 34.1 |
| 24.1° ± 0.2° | 16.1 |
| 24.8° ± 0.2° | 48.8 |

-continued

| Diffraction angel 2θ | Relative intensity % |
|---|---|
| 25.5° ± 0.2° | 11.1 |
| 26.8° ± 0.2° | 62.5 |
| 27.3° ± 0.2° | 16.7 |

Non-restrictively, in one typical embodiment of the present invention, the X-ray powder diffraction pattern of Form I is shown in FIG. 2.

Non-restrictively, the DSC thermogram of Form I is shown in FIG. 3.

Non-restrictively, the TGA thermogram of Form I is shown in FIG. 4.

Non-restrictively, the isothermal sorption plot of Form I is shown in FIG. 5.

Compared with the known Form A, Form I has the following beneficial properties:

1) According to the XRPD pattern, Form I has a higher crystallinity.
2) According to the DSC thermogram, Form I has a high melting point at 235° C.
3) According to the isothermal sorption plot, the weight change of Form I is less than 0.2% between 20 to 80% RH and is not hygroscopic.
4) According to Example 48, Form I still remained its original form and its purity essentially did not change after having been placed for 10 days at 60° C. dry condition and 40° C./75% RH (relative humidity) condition. Form I has better stability.
5) According to Comparative Example 1, the crystalline form of Form I remained unchanged after having been stirred for 3 days in water while the known Form A transformed to Form I. Form I has better stability in water.

The above advantageous properties of Form I show that, compared with the known Form A, Form I has high crystallinity, good stability, low hygroscopicity, better flowability and processing characteristics (processing such as filtrating, drying, weighing, screening, and so on), which are beneficial to improving the homogeneity of the pharmaceutical formulations, and may better ensure the pharmaceutically active ingredient itself and the formulations containing tipifarnib, avoid or reduce quality, safety and stability issues during drug manufacturing and/or storage, such as content uniformity and impurity issues, avoiding special and expensive package. Moreover, Form I has good stability in water, is more suitable for the wet granulation process of the solid dosage forms or the preparation of oral suspension dosage form, and can be kept stable during the manufacture and/or storage of the drug.

According to the objective of the present invention, the present invention provides a preparation method of Form I, characterized in that, the preparation method is selected from any one of the following methods, comprising:

1) Forming a suspension of tipifarnib solids in a solvent, stirring for crystallization and precipitation, and then separating crystals and drying to obtain Form I;
preferably, the solvent is selected from the group consisting of ethanol, n-propanol, water, nitromethane, acetone, ethyl acetate, isopropyl ether, methyl tert-butyl ether, tetrahydrofuran, acetonitrile, dichloromethane, n-heptane, and any mixture thereof, more preferably ethyl acetate, acetonitrile, methyl tert-butyl ether, n-propanol, or any mixture thereof;
preferably, the weight to volume ratio of tipifarnib solids to the solvent is from 5 mg/1 mL to 100 mg/1 mL, more preferably from 20 mg/1 mL to 50 mg/1 mL;
preferably, the stirring time is from 4 days to 5 days;
preferably, the stirring is carried out at 10° C. to 40° C.;
preferably, the drying temperature is from 10° C. to 40° C., the drying time is from 10 hours to 48 hours.

2) Forming a solution of tipifarnib solids in a solvent, then volatilizing to dryness to obtain Form I;
preferably, the solvent is selected from the group consisting of ketones, esters, n-propanol, sec-butanol, butanol, water, tetrahydrofuran, 1,4-dioxane, acetonitrile, dichloromethane, toluene and any mixture thereof, more preferably acetone, dichloromethane, water, acetonitrile or any mixture thereof;
preferably, the weight to volume ratio of tipifarnib solids to the solvent is from 5 mg/1 mL to 50 mg/1 mL, more preferably from 5 mg/1 mL to 25 mg/1 mL;
preferably, the volume ratio of the two solvents in the solvent mixture is from 1:3 to 3:1;
preferably, the volatilizing process is carried out at 25° C. to 40° C.

3) Forming a solution of tipifarnib solids in a solvent, cooling with stirring for crystallization and precipitation, and then separating crystals and drying to obtain Form I;
preferably, the solvent is selected from the group consisting of alcohols, ketones, esters, acetonitrile and any mixture thereof; more preferably acetone or isopropanol;
preferably, the weight to volume ratio of tipifarnib solids to the solvent is from 40 mg/1 mL to 150 mg/1 mL, more preferably from 40 mg/1 mL to 100 mg/1 mL;
preferably, the temperature of forming solution is from 60° C. to 75° C., more preferably from 60° C. to 70° C.;
preferably, the temperature of crystallization and precipitation is from −10° C. to 10° C., more preferably from −10° C. to 0° C.;
preferably, the crystallization time is from 1 hour to 10 hours.

4) Forming a solution of tipifarnib solids in a co-solvent, adding anti-solvent, stirring for crystallization and precipitation, and then separating crystals and drying to obtain Form I;
preferably, the co-solvent is selected from the group consisting of alcohols, acetone, ethyl acetate, tetrahydrofuran and nitromethane; more preferably methanol, ethanol, acetone or tetrahydrofuran;
preferably, the weight to volume ratio of tipifarnib solids to the co-solvent is from 10 mg/1 mL to 50 mg/1 mL, more preferably from 10 mg/1 mL to 25 mg/1 mL;
preferably, the anti-solvent is selected from the group consisting of water, isopropyl ether, and n-heptane;
preferably, the stirring time is from 3 minutes to 60 minutes;
preferably, the stirring is carried out at room temperature.

5) Forming a suspension of amorphous tipifarnib in a solvent, stirring for crystallization and precipitation, then separating crystals and drying to obtain Form I;
preferably, the solvent is selected from the group consisting of alcohols, ketones, esters, ethers, alkanes, tetrahydrofuran and acetonitrile; more preferably ethyl acetate or acetonitrile;
preferably, the weight to volume ratio of amorphous tipifarnib to the solvent is from 20 mg/1 mL to 100 mg/1 mL, more preferably from 20 mg/1 mL to 50 mg/1 mL;

preferably, the stirring time is from 10 minutes to 20 minutes, more preferably 10 minutes to 15 minutes.
preferably, the stirring is carried out at room temperature.

According to the objective of the invention, the second aspect of the invention is to provide a solid-state tipifarnib Form II (hereinafter referred to as "Form II") and its preparation method.

The present invention provides Form II with its structure shown in the formula (II) below:

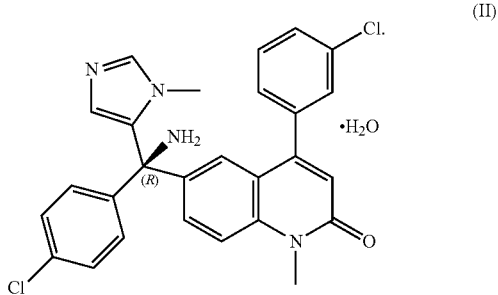

(II)

Form II is monohydrate, using Cu-Kα radiation, the X-ray powder diffraction pattern of Form II, expressed as 2θ angles, has the following characteristic peaks: 5.3°±0.2°, 6.8°±0.2°, 8.5°±0.2°, 16.3°±0.2°, 18.0°±0.2° and 20.9°±0.2°.

In a preferred embodiment of the present invention, the X-ray powder diffraction pattern of Form II, expressed as 2θ angles, has the following characteristic peaks: 5.3°±0.2°, 6.8°±0.2°, 8.5°±0.2°, 12.8°±0.2°, 13.8°±0.2°, 16.3°±0.2°, 16.9°±0.2°, 17.1°±0.2°, 18.0°±0.2°, 18.5°±0.2°, 20.9°±0.2° and 27.9°±0.2°.

In a further preferred embodiment of the present invention, the X-ray powder diffraction pattern of Form II, expressed as 2θ angles, has the following characteristic peaks and relative intensities:

| Diffraction angel 2θ | Relative intensity % |
| --- | --- |
| 5.3° ± 0.2° | 43.3 |
| 6.8° ± 0.2° | 100 |
| 8.5° ± 0.2° | 44.4 |
| 12.8° ± 0.2° | 16.2 |
| 13.8° ± 0.2° | 12.9 |
| 16.3° ± 0.2° | 45.7 |
| 16.9° ± 0.2° | 26.5 |
| 17.1° ± 0.2° | 21.2 |
| 18.0° ± 0.2° | 78.2 |
| 18.5° ± 0.2° | 21.3 |
| 20.4° ± 0.2° | 8.4 |
| 20.9° ± 0.2° | 28.1 |
| 21.5° ± 0.2° | 6.9 |
| 21.9° ± 0.2° | 9.9 |
| 22.3° ± 0.2° | 6.6 |
| 23.6° ± 0.2° | 11.6 |
| 24.1° ± 0.2° | 9.8 |
| 27.1° ± 0.2° | 11.3 |
| 27.9° ± 0.2° | 15.7 |
| 28.9° ± 0.2° | 12.4 |
| 30.8° ± 0.2° | 10.4. |

Non-restrictively, in one typical embodiment of the present invention, the X-ray powder diffraction pattern of Form II is shown in FIG. 6.

Non-restrictively, the DSC thermogram of Form II is shown in FIG. 7.

Non-restrictively, the TGA thermogram of Form II is shown in FIG. 8.

Compared with the known Form A, Form II has the following beneficial properties:
1) According to the XPRD pattern, Form II has a higher crystallinity.
2) According to the DSC thermogram, Form II has a high melting point at 235° C.
3) According to Example 48, Form II still remained its original form and its purity essentially did not change after having been placed for 10 days at 60° C. dry condition and 40° C./75% RH condition, respectively. Form II has better stability.
4) According to Comparative Example 1, the crystalline form of Form II remained unchanged after having been stirred for 3 days in water while the known Form A transformed to Form I. Form II has better stability in water.

The above advantageous properties of Form II show that, compared with the known Form A, Form II has high crystallinity, good stability, better flowability and processing characteristics (processing such as filtrating, drying, weighing, screening, and so on), which are beneficial to improving the homogeneity of the pharmaceutical formulations, and may better ensure the pharmaceutically active ingredient itself and the formulations containing tipifarnib, avoid or reduce quality, safety and stability issues during drug manufacturing and/or storage, such as content uniformity and impurity issues, avoiding special and expensive package. Moreover, Form II has good stability in water, is more suitable for the wet granulation process of the solid dosage form or the preparation of oral suspension dosage form, and can be kept stable during the manufacture and/or storage of the drug.

According to the objective of the present invention, the present invention provides a preparation method of Form II, characterized in that, the preparation method is selected from any one of the following methods, comprising:
1) Forming a solution of tipifarnib solids in a solvent, then volatilizing to dryness to obtain Form II;
   preferably, the solvent is selected from the group consisting of methanol, ethanol, trifluoroethanol and any mixture thereof, more preferably methanol;
   preferably, the weight to volume ratio of tipifarnib solids to the solvent is from 10 mg/1 mL to 50 mg/1 mL, more preferably from 10 mg/1 mL to 30 mg/1 mL;
   preferably, the volatilizing process is carried out at 10° C. to 40° C., more preferably 10° C. to 30° C.
2) Forming a suspension of amorphous tipifarnib solids in a solvent, stirring for crystallization and precipitation, and then separating crystals and drying to obtain Form II;
   preferably, the solvent is selected from the group consisting of an alcohol-water mixture, a ketone-water mixture, a tetrahydrofuran-water mixture, a 1,4-dioxane-water mixture, an acetonitrile-water mixture, and a dimethyl sulfoxide-water mixture, more preferably a dimethyl sulfoxide-water mixture.
   preferably, the volume percentage of water in the solvent is from 50% to 100%, more preferably from 85% to 100%;
   preferably, the weight to volume ratio of tipifarnib solids to the solvent is from 25 mg/1 mL to 100 mg/1 mL, more preferably from 25 mg/1 mL to 35 mg/1 mL;
   preferably, the stirring time is from 10 minutes to 20 minutes, more preferably from 10 minutes to 15 minutes;

preferably, the stirring temperature is from 4° C. to 25° C.;
preferably, the drying temperature is from 10° C. to 30° C., the drying time is from 10 hours to 24 hours.
3) Placing amorphous tipifarnib solids in a humidity desiccator to obtain Form II;
preferably, the relative humidity in the humidity desiccator is from 85% to 100%, more preferably 97%;
preferably, the placing time is from 1 day to 7 days, more preferably 1 day.

According to the objective of the invention, the third aspect of the invention is to provide a solid-state tipifarnib Form III (hereinafter referred to as "Form III") and its preparation method.

The present invention provides Form III with its structure shown in the formula (III) below:

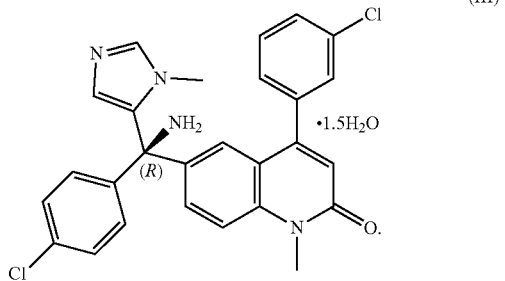

Form III is sesquihydrate, using Cu-Kα radiation, the X-ray powder diffraction pattern of Form III, expressed as 2θ angles, has the following characteristic peaks: 6.2°±0.2°, 8.8°±0.2°, 15.9°±0.2° and 18.2°±0.2°.

In a preferred embodiment of the present invention, the X-ray powder diffraction pattern of Form III, expressed as 2θ angles, has the following characteristic peaks: 6.2°±0.2°, 8.8°±0.2°, 13.2°±0.2°, 15.9°±0.2°, 18.2°±0.2°, 19.8°±0.2°, 22.2°±0.2° and 26.1°±0.2°.

In a further preferred embodiment of the present invention, the X-ray powder diffraction pattern of Form III, expressed as 2θ angles, has the following characteristic peaks and relative intensities:

| Diffraction angel 2θ | Relative intensity % |
|---|---|
| 6.2° ± 0.2° | 10.2 |
| 8.8° ± 0.2° | 100 |
| 12.4° ± 0.2° | 4.1 |
| 13.2° ± 0.2° | 7.3 |
| 15.9° ± 0.2° | 23.9 |
| 18.2° ± 0.2° | 33.2 |
| 19.8° ± 0.2° | 8.7 |
| 21.0° ± 0.2° | 3.7 |
| 22.2° ± 0.2° | 10.8 |
| 22.8° ± 0.2° | 4.4 |
| 24.1° ± 0.2° | 6.9 |
| 26.1° ± 0.2° | 9.9 |
| 27.6° ± 0.2° | 6.6 |

Non-restrictively, in one typical embodiment of the present invention, the X-ray powder diffraction pattern of Form III is shown in FIG. 9.

Non-restrictively, the DSC thermogram of Form III is shown in FIG. 10.

Non-restrictively, the TGA thermogram of Form III is shown in FIG. 11.

Compared with the known Form A, Form III has the following beneficial properties:
1) According to the XRPD pattern, Form III has a higher crystallinity.
2) According to Example 48, Form III remained its original form and its purity essentially did not change after having been placed for 10 days at 60° C. dry condition and 40° C./75% RH condition. Form III has better stability.
3) According to Comparative Example 1, the crystalline form of Form III remained unchanged after having been stirred for 3 days in water while the known Form A transformed to Form I. Form III has better stability in water.

The above advantageous properties of Form III show that, compared with the known Form A, Form III has high crystallinity, good stability, low hygroscopicity, better flowability and processing characteristics (processing such as filtrating, drying, weighing, screening, and so on), which are beneficial to improving the homogeneity of the pharmaceutical formulations, and may better ensure the pharmaceutically active ingredient itself and the formulations containing tipifarnib, avoid or reduce quality, safety and stability issues during drug manufacturing and/or storage, such as content uniformity and impurity issues, avoiding special and expensive package. Moreover, Form III has good stability in water, is more suitable for the wet granulation process of the solid dosage form or the preparation of oral suspension dosage form, and can be kept stable during the manufacture and/or storage of the drug.

According to the objective of the present invention, the present invention provides a preparation method of Form III, characterized in that, the preparation method is selected from any one of the following methods, comprising:
1) Forming a solution of tipifarnib solids in a solvent, cooling with stirring for crystallization and precipitation, and then separating crystals and drying to obtain Form III;
preferably, the solvent is a water-acetonitrile mixture or a water-acetone mixture;
preferably, the volume percentage of water in the solvent is from 30% to 50%;
preferably, the weight to volume ratio of tipifarnib solids to the solvent is from 14 mg/1 mL to 25 mg/1 mL;
preferably, the temperature of forming solution is from 60° C. to 70° C.;
preferably, the temperature of crystallization and precipitation is from −10° C. to 0° C.;
preferably, the crystallization time is from 1 hour to 24 hours;
preferably, the drying temperature is from 10° C. to 40° C., the drying time is from 10 hours to 24 hours.
2) Forming a solution of tipifarnib solids in a co-solvent, adding an anti-solvent, stirring for crystallization and precipitation, and then separating crystals and drying to obtain Form III;
preferably, the co-solvent is selected from the group consisting of acetonitrile, 1,4-dioxane, butanone and isopropyl acetate, more preferably acetonitrile or 1,4-dioxane;
preferably, the weight to volume ratio of tipifarnib solids to the co-solvent is from 2 mg/1 mL to 25 mg/1 mL, more preferably 10 mg/1 mL to 25 mg/1 mL;
preferably, the anti-solvent is water or n-heptane;
preferably, the stirring time is from 1 hour to 24 hours;
preferably, the stirring is carried out at room temperature;

preferably, the drying temperature is from 10° C. to 40° C., the drying time is from 10 hours to 24 hours.

3) Forming a solution of tipifarnib solids in a solvent, then volatilizing to dryness to obtain Form III;

preferably, the solvent is selected from the group consisting of a nitromethane-water mixture, a butanone-water mixture, an acetonitrile-water mixture, a tetrahydrofuran-water mixture, and a 1,4-dioxane-water mixture, more preferably a butanone-water mixture or a nitromethane-water mixture;

preferably, the weight to volume ratio of tipifarnib solids to the solvent is from 5 mg/l mL to 10 mg/l mL;

preferably, the volume percentage of water in the solvent is from 1% to 10%;

preferably, the volatilizing temperature is from 10° C. to 30° C., more preferably from 20° C. to 30° C.

According to the objective of the invention, the fourth aspect of the invention is to provide a solid-state tipifarnib Form IV (hereinafter referred to as "Form IV") and its preparation method.

The present invention provides Form IV with its structure shown in the formula (I) below:

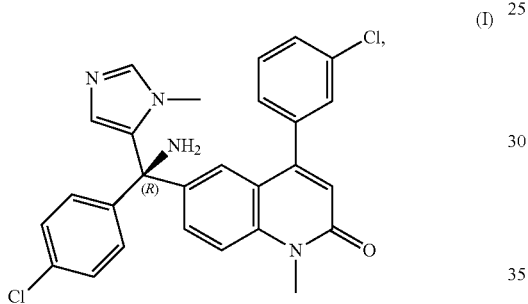

(I)

using Cu-Kα radiation, the X-ray powder diffraction pattern of Form IV, expressed as 2θ angles, has the following characteristic peaks: 7.5°±0.2°, 13.9°±0.2°, 15.8°±0.2°, 16.5°±0.2°, 17.4°±0.2° and 18.1°±0.2°.

In a preferred embodiment of the present invention, the X-ray powder diffraction pattern of Form IV, expressed as 2θ angles, has the following characteristic peaks: 7.5°±0.2°, 13.9°±0.2°, 15.4°±0.2°, 15.8°±0.2°, 16.5°±0.2°, 17.4°±0.2°, 18.1°±0.2°, 20.7°±0.2°, 21.6°±0.2°, 24.3°±0.2°, 26.5°±0.2° and 29.1°±0.2°.

In a further preferred embodiment of the present invention, the X-ray powder diffraction pattern of Form IV, expressed as 2θ angles, has the following characteristic peaks and relative intensities:

| Diffraction angel 2θ | Relative intensity % |
|---|---|
| 7.5° ± 0.2° | 51.8 |
| 13.9° ± 0.2° | 22.1 |
| 15.4° ± 0.2° | 20.4 |
| 15.8° ± 0.2° | 42.3 |
| 16.5° ± 0.2° | 100 |
| 17.4° ± 0.2° | 24.7 |
| 18.1° ± 0.2° | 23 |
| 18.9° ± 0.2° | 13.4 |
| 20.7° ± 0.2° | 18.4 |
| 21.6° ± 0.2° | 11.1 |
| 23.0° ± 0.2° | 16.7 |
| 24.3° ± 0.2° | 18 |
| 24.7° ± 0.2° | 13 |
| 25.1° ± 0.2° | 16.1 |

-continued

| Diffraction angel 2θ | Relative intensity % |
|---|---|
| 25.9° ± 0.2° | 14.5 |
| 26.5° ± 0.2° | 21.5 |
| 27.5° ± 0.2° | 19.1 |
| 29.1° ± 0.2° | 24.1. |

Non-restrictively, in one typical embodiment of the present invention, the X-ray powder diffraction pattern of Form IV is shown in FIG. 12.

Non-restrictively, the DSC thermogram of Form IV is shown in FIG. 13.

Non-restrictively, the TGA thermogram of Form IV is shown in FIG. 14.

Compared with the known Form A, Form IV has the following beneficial properties:

1) According to the XRPD pattern, Form IV has a higher crystallinity.
2) According to the DSC thermogram, Form IV has a high melting point at 235° C.
3) According to Comparative Example 1, the crystalline form of Form IV remained unchanged after having been stirred for 3 days in water while the known Form A transformed to Form I. Form IV has better stability in water.
4) According to Example 48, Form IV still remained its original form and its purity essentially did not change after having been placed for 10 days at 60° C./dry condition and 40° C./75% RH condition. Form IV has better stability.

The above advantageous properties of Form IV show that, compared with the known Form A, Form IV has high crystallinity, good stability, better flowability and processing characteristics (processing such as filtrating, drying, weighing, screening, and so on), which are beneficial to improving the homogeneity of the pharmaceutical formulations, and may better ensure the pharmaceutically active ingredient itself and the formulations containing tipifarnib, avoid or reduce quality, safety and stability issues during drug manufacturing and/or storage, such as content uniformity and impurity issues, avoiding special and expensive package. Moreover, Form IV has high solubility, and better dissolution and bioavailability.

According to the objective of the present invention, the present invention provides a preparation method of Form IV, characterized in that, the preparation method comprises the following steps:

Forming a solution of tipifarnib solids in a solvent, then volatilizing to dryness to obtain Form IV;

preferably, the solvent is ethanol or chloroform;

preferably, the weight to volume ratio of tipifarnib solids to the solvent is from 10 mg/l mL to 25 mg/l mL;

preferably, the volatilizing process is carried out at 40° C. to 50° C.;

According to the objective of the present invention, the fifth aspect of the present invention is to provide a solid-state tipifarnib Form V (hereinafter referred to as "Form V") and its preparation method.

Using Cu-Kα radiation, the X-ray powder diffraction pattern of Form V, expressed as 2θ angles, has the following characteristic peaks: 6.6°±0.2°, 7.8°±0.2°, 8.5°±0.2°, 13.4°±0.2°, 15.1°±0.2°, 15.9°±0.2°, 17.2°±0.2°, 17.7°±0.2°, 17.9°±0.2°, 18.5°±0.2°, 20.2°±0.2° and 20.9°±0.2°.

Non-restrictively, in one typical embodiment of the present invention, the X-ray powder diffraction pattern of Form V is shown in FIG. 15.

The present invention also provides a preparation method of Form V, which comprises the following steps: heating Form II to obtain Form V.

Preferably, the heating rate is from 20° C./minute to 30° C./minute;

Preferably, the end-point temperature of the heating is from 80° C. to 120° C.

According to the objective of the present invention, the sixth aspect of the present invention is to provide amorphous tipifarnib and its preparation method.

Non-restrictively, in one typical embodiment of the present invention, the X-ray powder diffraction pattern of amorphous tipifarnib is shown in FIG. 16.

The present invention provides a preparation method of amorphous tipifarnib, which comprises the following steps: forming a solution of tipifarnib solids in a solvent, concentrating the solvent under vacuum to dryness to obtain amorphous tipifarnib.

Preferably, the solvent is dichloromethane;

Preferably, the weight to volume ratio of tipifarnib solids to the solvent is from 50 mg/l mL to 100 mg/l mL;

Preferably, the concentrating under vacuum is carried out at 30° C. to 40° C.

In the preparation methods of tipifarnib forms of the present invention, the starting material "tipifarnib" may be a disclosed tipifarnib compound or the crystalline forms thereof, for example, but not limited to, tipifarnib prepared according to any one of the preparation methods in patent documents CN1101392C, CN100567292C and CN1246318C. These patent documents are incorporated herein by reference in their entirety.

The terms used in the present invention include:

The "room temperature" is a temperature between 10° C. to 30° C.

The "overnight" refers to a period of time spanning the night, usually 10 hours to 16 hours.

"Stirring" may be carried out by a conventional method in the art, such as magnetic stirring, mechanical stirring, and the stirring speed is 50 r/min to 1800 r/min, preferably 300 r/min to 900 r/min.

"Separation" may be carried out by a conventional method in the art, such as centrifugation or filtration. Preferred method is vacuum filtration, generally at a pressure less than atmospheric pressure at room temperature, preferably less than 0.09 MPa.

"Drying" may be performed by conventional methods in the art, such as room temperature drying, forced air drying or vacuum drying. Drying instruments and methods are unrestricted, and may be fume hood, blast oven, spray drying, fluidized bed drying or vacuum oven, and may be performed under reduced pressure or atmospheric pressure, pressure less than 0.09 MPa is preferred. The drying temperature is from 10° C. to 40° C., and the drying time is from 10 hours to 72 hours, preferably from 2 hours to 24 hours, more preferably from 2 hours to 8 hours.

The vacuum concentration refers to the operation of a rotary evaporator to volatilize solvent under pressure less than atmospheric pressure. The experimental temperature is from 10° C. to 50° C., and the rotational speed is from 50 rpm to 200 rpm.

In the present invention, "crystal" or "crystalline form" refers to that characterized by X-ray powder diffraction pattern, having a unique ordered molecular arrangement or configuration within the crystalline lattice. It is known to those skilled in the field that the experimental error depends on instrumental conditions, sample preparation and sample purity. The 2θ angle of the peaks in the XRPD pattern may change with the change of instrument and samples. The difference of peak position may vary by 1°, 0.8°, 0.5°, 0.3°, 0.1°, etc., depending on the instruments and samples, and ±0.2° in error is usually allowed. Therefore the difference in peak position should not be regarded as the only factor. The relative intensity of peaks may change with the change of sample, sample preparation, and other experimental conditions. Therefore, the order of peak intensities should not be regarded as the only or the determining factor. Due to the effect of experimental factors including sample height, peak position may shift. Generally, a small amount of peak shifting is acceptable. Hence, it is easily understood for those skilled in the field that any crystalline form having the same or similar x-ray powder diffraction pattern as that of the crystalline form in the present invention should be within the scope of the present invention. "Single crystalline form" refers to a crystalline form confirmed by x-ray powder diffraction as a single form.

Tipifarnib forms of the present invention are substantially pure, single, and substantially free of any other crystalline or amorphous forms. As used herein, "substantially pure" when used in reference to a new crystalline form means that the new crystalline form comprises at least 80% by weight of the present compound, more preferably at least 90% (by weight), especially at least 95% (by weight), especially at least 99% (by weight).

The seventh aspect of the invention is to provide a pharmaceutical composition, which comprises a therapeutically and/or preventively effective amount of pharmaceutical active ingredient selected from the crystalline forms of tipifarnib of the present invention or the crystalline forms of tipifarnib prepared by the preparation methods of the present invention, and at least one pharmaceutically acceptable excipient. Wherein tipifarnib forms of the present invention include Form I, Form II, Form III and Form IV. In addition, the pharmaceutical composition may also comprise other pharmaceutically acceptable crystalline forms (e.g. Form V) or amorphous forms of tipifarnib.

The excipients of pharmaceutical composition are known to those skilled in the field, and the selection of the type, usage and amount of the excipients is also known to those skilled in the field. For example, they include carbohydrate, cellulose and its derivative, starch or modified starch, adhesives such as microcrystalline cellulose, ethyl cellulose, hydroxymethyl cellulose, hydroxypropyl methyl cellulose, hydroxyethyl cellulose, disintegrants such as sodium glycolate starch, crospovidone, croscarmellose, sodium carboxymethylcellulose, cornstarch, lubricant such as stearic acid, magnesium stearate, sodium stearyl fumarate, polyethyleneglycol, filler such as kaolin.

The administration route of pharmaceutical composition includes oral administration, intravenous subcutaneous injection, tissue injection, transdermal administration, rectal administration, etc. The pharmaceutical composition may be prepared as a certain dosage form depending on the route of administration or need, and may be solid or liquid. Solid oral dosage forms, including, for example, tablets, powders, pills and capsules; liquid oral dosage forms, including, for example, solutions, syrups, suspensions and elixirs, injectable preparations, including, for example, solutions and suspensions, spray or epithelial administration.

The formulation may be suitable for immediate, sustained or controlled release of the active ingredient of the drug. It may be a conventional, dispersible, chewable, buccal soluble or rapidly dissolvable formulation.

The pharmaceutical composition may be prepared by the method commonly known to those skilled in the art. In preparation of the pharmaceutical composition, the tipifarnib forms of the present invention (include Form I, Form II, Form II and Form IV) are mixed with one or more pharmaceutically acceptable excipients, optionally with other pharmaceutically acceptable polymorphs and amorphous form of tipifarnib, optionally with one or more other active ingredients. Solid formulations may be prepared by direct mixing, granulation and other processes.

According to the objective of the present invention, the present invention provides the crystalline forms of tipifarnib or the crystalline forms of tipifarnib prepared by the preparation methods of the present invention in the preparation of a medicament for the treatment and/or prevention of abnormal cell growth diseases; the diseases include but not limited to solid tumors and blood cancers associated with RAS mutation or over expression, such as lung cancer, pancreatic cancer, colon cancer, thyroid follicular cancer, myelodysplastic syndrome, interstitial cell tumor, melanoma, teratoma, neuroblastoma, glioma, epidermal cancer such as head and neck squamous cell carcinoma, salivary gland cancer, skin benign tumor, breast cancer, kidney cancer, bone cancer, ovarian cancer, bladder cancer, liver cancer, multiple neurofibromatosis, hematologic lymphoma such as peripheral T lymphoma, myeloid leukemia, myelodysplastic syndrome (MDS), chronic granulocytic leukemia, and so on. According to an objective of the present invention, the present invention provides a method of treating and/or preventing of abnormal cell growth diseases, the method comprising administering to a patient in need thereof a therapeutically and/or prophylactically effective amount of the foregoing pharmaceutical compositions of Form I, Form II, Form III and Form IV. The diseases are the same as those mentioned above in this specification.

Active compounds are usually effective in large doses. In general it is contemplated that an effective amount would be from 0.0001 mg/kg to 100 mg/kg body weight, and in particular from 0.001 mg/kg to 10 mg/kg body weight. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage from.

SPECIFIC IMPLEMENTATIONS

The following examples help to further understand the present invention, but are not intended to limit the contents of the present invention.

Instruments and characterization methods:

X-ray powder diffraction (XRPD): performed on Bruder D8 Advance diffractometer. The samples were tested at room temperature under the following conditions: scan range 3-40° 2θ, step size 0.02° 2θ, and speed 0.2 s/step.

Differential thermal analysis data were collected on TA Instruments Q200 MDSC. Method: place 1 mg to 10 mg sample into an sealed aluminum pan, ramp to 250° C. at a rate of 10° C./min under the protection of dry $N_2$ purge at 40 mL/min.

Thermogravimetric analysis data were collected on TA Instruments Q500 TGA. Method: place 5 mg to 15 mg sample into a platinum pan, use high resolution method, ramp to 350° C. at a rate of 10° C./min under the protection of dry $N_2$ purge at 40 mL/min.

Infrared spectrometry (IR) data were collected using Burker Tensor 27 FT-IR. The instrument control software and data analysis software are OPUS. Usually, ATR equipment is used to collect infrared absorption spectra in the range of 600 $cm^{-1}$-4000 $cm^{-1}$, the scanning time for sample and blank background is 16 seconds, and the instrument resolution is 4 $cm^{-1}$.

Dynamic vapor sorption data and isothermal sorption data were collected on TA Instruments Q5000 TGA. Method: place 1 mg to 10 mg sample into a platinum pan; the weight change of the sample during the change in relative humidity from 0% to 80% to 0% was measured.

$^1$H Nuclear magnetic resonance spectrum ($^1$H-NMR) data were collected on Bruker Avance II DMX 400 MHz nuclear magnetic resonance spectrometer. Method: place 1 mg to 5 mg sample and dissolve it into a nuclear magnetic sample tube with 0.5 mL deuterated reagent for detection.

Unless particularly specified, all Examples were conducted at room temperature, solvent ratio is volume ratio.

Unless particularly specified, all reagents used in the Examples were commercially available.

Preparation Example 1

Tipifarnib was prepared by referencing the methods described in the preparation, resolution and purification steps of the compound (I) in the specification of patent document CN1246318C.

Figure 1:
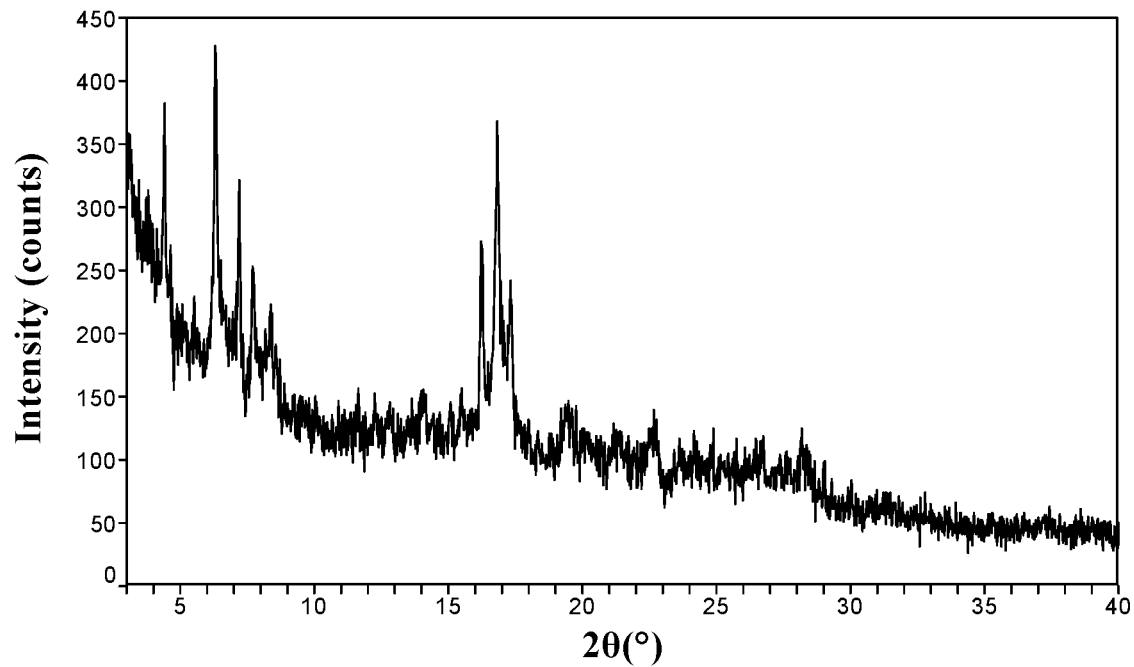
FIG. 1 is the XPRD pattern of tipifarnib prepared according to patent document CN1246318C.

The XRPD pattern is shown in FIG. 1.

The above characterization results indicate that tipifarnib obtained by the method described in the preparation of compound (I) of patent document CN1246318C is Form A with low crystallinity.

Example 1

Took 200 mg tipifarnib of Preparation Example 1, added 2.0 mL dichloromethane to obtain a clear solution, concentrated the solution under vacuum at 40° C. to obtain amorphous tipifarnib; 90% yield.

Figure 16:
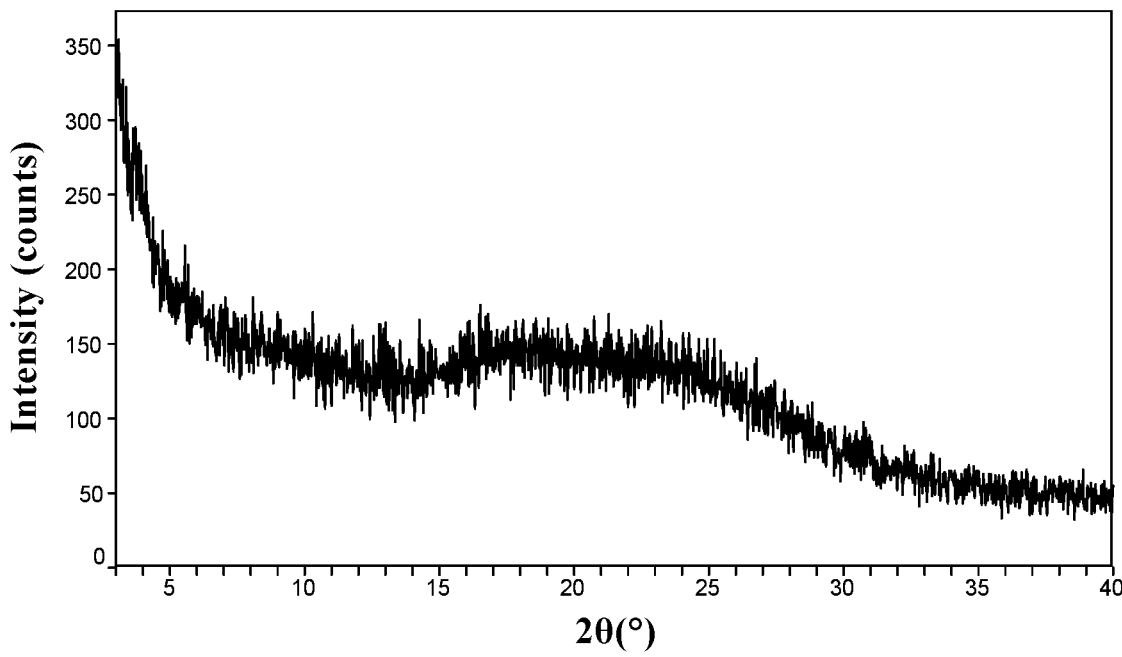
FIG. 16 is the XPRD pattern of amorphous tipifarnib of the present invention.

The XRPD pattern is shown in FIG. 16.

Example 2

Took 20 mg tipifarnib of Preparation Example 1, added 1.0 mL ethyl acetate to obtain a suspension, stirred at 10° C. for crystallization and precipitation for 4 days, vacuum filtrated, and then vacuum dried at 40° C. for 10 hours to obtain 18 mg tipifarnib Form I; 90% yield.

Figure 2:
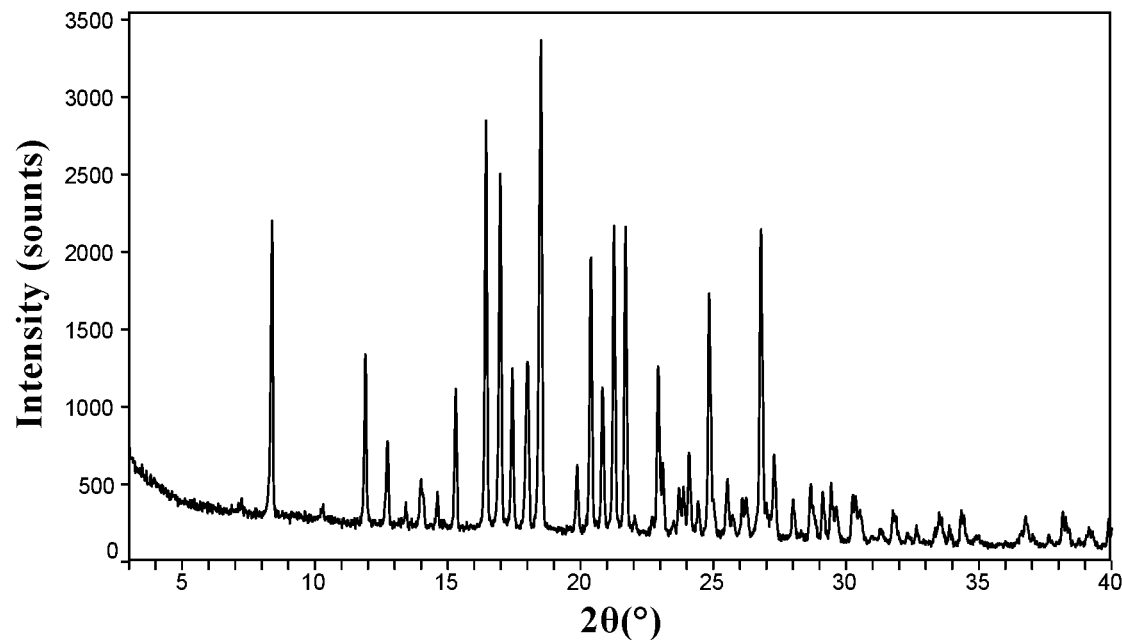
FIG. 2 is the XPRD pattern of tipifarnib Form I of the present invention.
Figure 3:
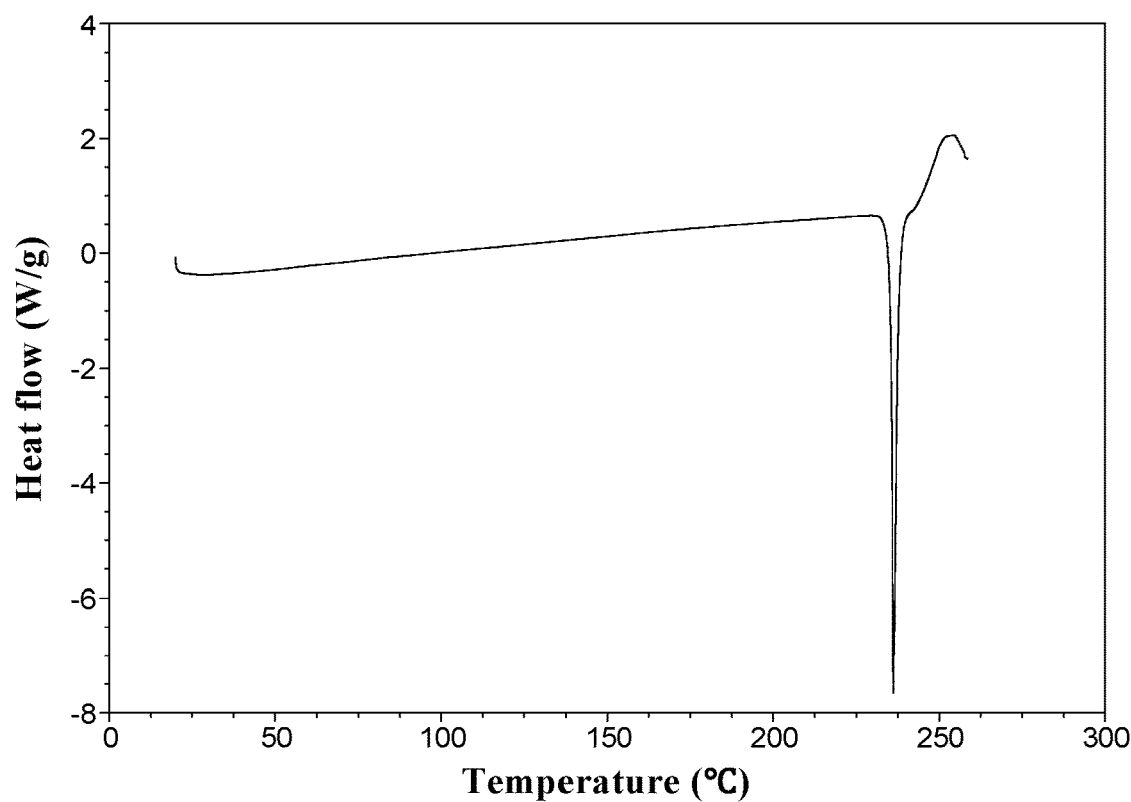
FIG. 3 is the DSC thermogram of tipifarnib Form I of the present invention.
Figure 4:
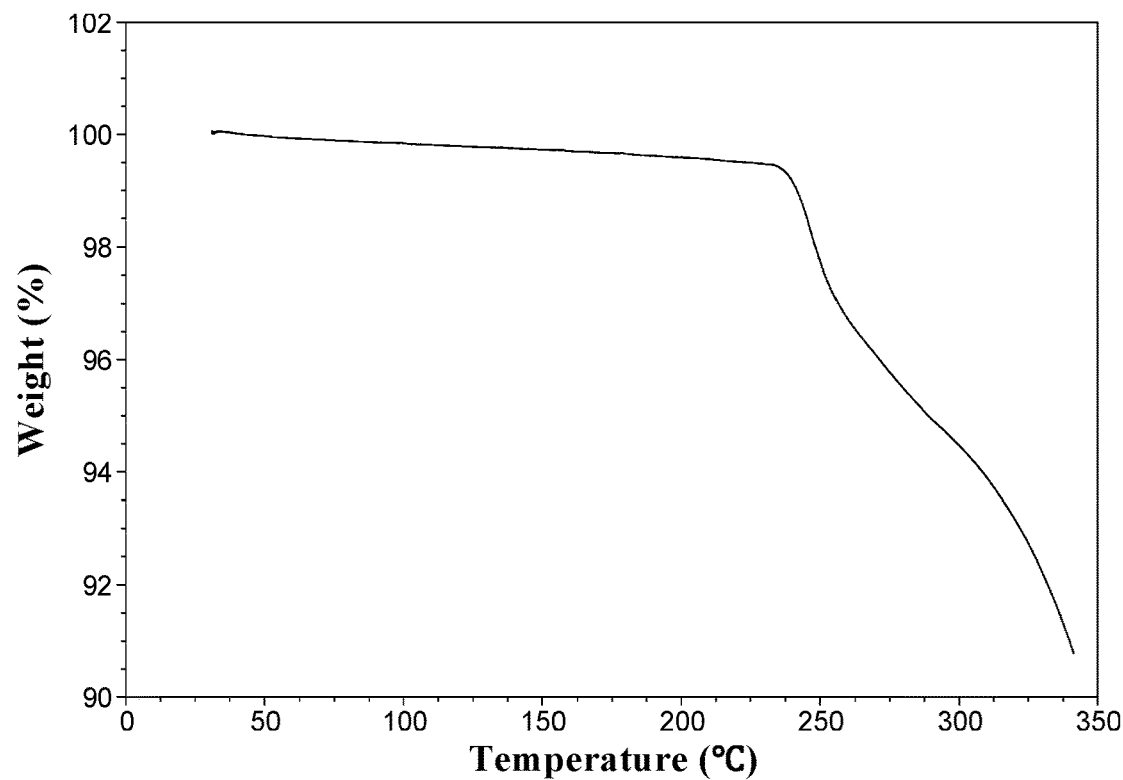
FIG. 4 is the TGA thermogram of tipifarnib Form I of the present invention.
Figure 5:
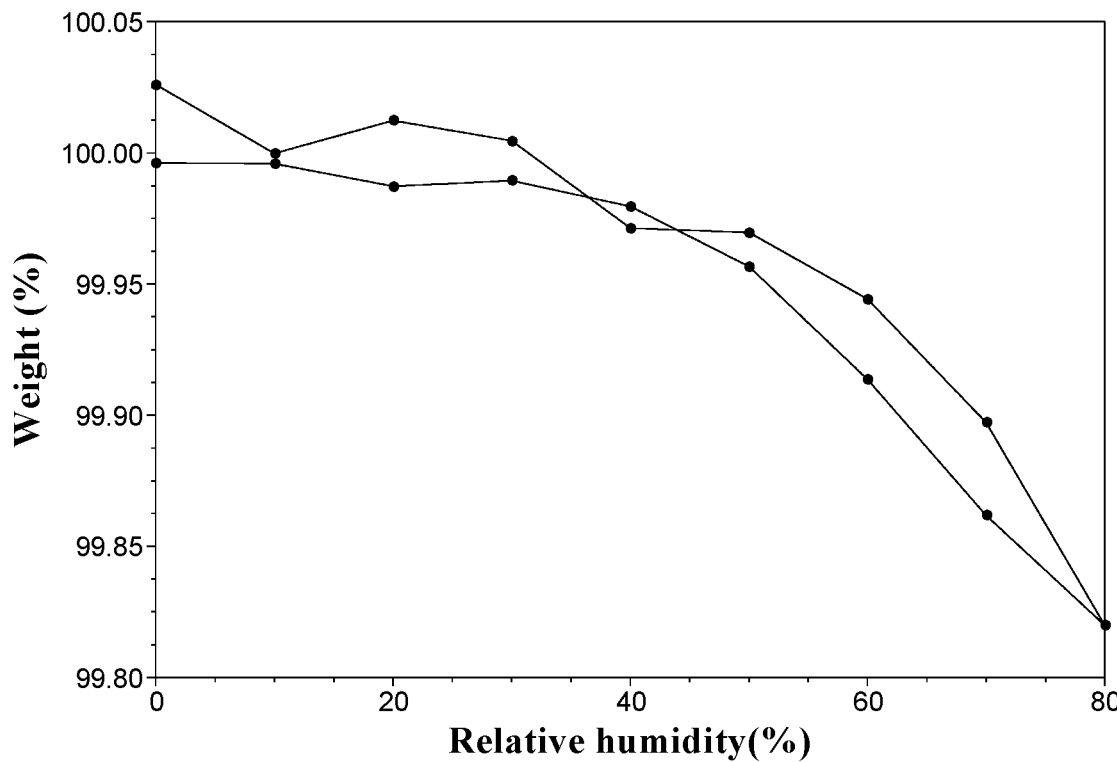
FIG. 5 is the isothermal sorption plot of tipifarnib Form I of the present invention.

Its XRPD pattern is shown in FIG. 2.
Its DSC thermogram is shown in FIG. 3.
Its TGA thermogram is shown in FIG. 4.
Its isothermal sorption plot is shown in FIG. 5.

Example 3

Took 100 mg tipifarnib of Preparation Example 1, added 0.4 mL acetonitrile and 1.6 mL methyl tert-butyl ether to obtain a suspension, stirred at 40° C. for crystallization and precipitation for 5 days, vacuum filtrated, and then vacuum dried at 60° C. for 48 hours to obtain 88 mg tipifarnib Form I; 88% yield.

Example 4

Took 30 mg tipifarnib of Preparation Example 1, added 0.3 mL n-propanol to obtain a suspension, stirred at 25° C. for crystallization and precipitation for 4 days, vacuum filtrated, and then vacuum dried at 40° C. for 24 hours to obtain 25 mg tipifarnib Form I; 83.3% yield.

Example 5

Took 40 mg tipifarnib of Preparation Example 1, added 0.5 mL ethanol to obtain a suspension, stirred at 30° C. for crystallization and precipitation for 4 days, vacuum filtrated, and then vacuum dried at 50° C. for 30 hours to obtain 28 mg tipifarnib Form I; 70% yield.

Example 6

Form I can also be obtained by replacing the solvent in Example 5 with the following table.

| Experiment Number | Solvent 1 | Solvent 2 |
|---|---|---|
| Experiment 1 | Ethanol | Nitromethane |
| Experiment 2 | Ethanol | Ethyl acetate |
| Experiment 3 | Ethanol | n-Heptane |
| Experiment 4 | Water | Acetone |
| Experiment 5 | Water | Tetrahydrofuran |
| Experiment 6 | Dichloromethane | Ethyl acetate |
| Experiment 7 | n-Heptane | Isopropyl ether |

Example 7

Took 10 mg tipifarnib of Preparation Example 1, added 2.0 mL acetone to obtain a clear solution, volatilized at 25° C. to dryness to obtain 9.5 mg tipifarnib Form I; 95% yield.

Example 8

Took 10 mg tipifarnib of Preparation Example 1, added 0.4 mL dichloromethane to obtain a clear solution, volatilized at 40° C. to dryness to obtain 9.6 mg tipifarnib Form 1; 96% yield.

Example 9

Took 10 mg tipifarnib of Preparation Example 1, added 1.0 mL acetonitrile/water (3:1) to obtain a clear solution, volatilized at 40° C. to dryness to obtain 8.9 mg tipifarnib Form I; 89% yield.

Example 10

Took 50 mg tipifarnib of Preparation Example 1, added 1.0 mL methanol/acetone (3:1) to obtain a clear solution, volatilized at 30° C. to dryness to obtain 40 mg tipifarnib Form 1; 80% yield.

Example 11

Form I can also be obtained by replacing the solvents in Example 10 with the following table.

| Experiment Number | Solvent 1 | Solvent 2 |
|---|---|---|
| Experiment 1 | Methanol | Water |
| Experiment 2 | Methanol | Butanone |
| Experiment 3 | Ethanol | Ethyl acetate |
| Experiment 4 | Isopropanol | Isopropyl acetate |
| Experiment 5 | sec-Butanol | — |
| Experiment 6 | Tetrahydrofuran | Water |
| Experiment 7 | 1,4-dioxane | — |
| Experiment 8 | Acetonitrile | Toluene |

Example 12

Took 200 mg tipifarnib of Preparation Example 1, added 0.5 mL acetone at 60° C. to obtain a solution, stirred at −10° C. for 10 hours for crystallization and precipitation, vacuum filtrated, and then vacuum dried at room temperature overnight to obtain 17.5 mg tipifarnib Form I; 88% yield.

Example 13

Took 30 mg tipifarnib of Preparation Example 1, added 0.3 mL isopropanol at 70° C. to obtain a solution, stirred at 0° C. for 1 hour for crystallization and precipitation, vacuum filtrated, and then vacuum dried at room temperature overnight to obtain 26 mg tipifarnib Form I; 87% yield.

Example 14

Took 150 mg tipifarnib of Preparation Example 1, added 1.0 mL methanol at 75° C. to obtain a solution, stirred at 10° C. for 2 hours for crystallization and precipitation, vacuum filtrated, and then vacuum dried at room temperature overnight to obtain 110 mg tipifarnib Form I; 73% yield.

Example 15

Form I can also be obtained by replacing the solvent in Example 14 with the following table.

| Experiment Number | Solvent 1 | Solvent 2 |
|---|---|---|
| Experiment 1 | Methanol | Butanone |
| Experiment 2 | Ethanol | Ethyl acetate |
| Experiment 3 | n-Propanol | Isopropyl acetate |
| Experiment 4 | sec-butanol | — |
| Experiment 5 | n-Butanol | — |
| Experiment 6 | Acetonitrile | — |
| Experiment 7 | Acetonitrile | Ethyl acetate |
| Experiment 8 | Acetonitrile | Acetone |

Example 16

Placed 10 mg tipifarnib of Preparation Example 1 in 0.4 mL methanol to obtain a solution, added 5.2 mL isopropyl ether, stirred at room temperature for 3 minutes for crystallization and precipitation, vacuum filtrated, and then vacuum dried at room temperature for 48 hours to obtain 8.4 mg tipifarnib Form I; 84% yield.

Example 17

Placed 10 mg tipifarnib of Preparation Example 1 in 0.4 mL tetrahydrofuran to obtain a solution, added 4.0 mL n-heptane, stirred for 60 minutes for crystallization and precipitation, vacuum filtrated, and then vacuum dried at room temperature for 24 hours to obtain 7.8 mg tipifarnib Form I; 78% yield.

Example 18

Placed 10 mg tipifarnib of Preparation Example 1 in 1.0 mL acetone to obtain a solution, added 5.0 mL isopropyl ether, stirred for 30 minutes for crystallization and precipitation, vacuum filtrated, and then vacuum dried at room temperature for 10 hours to obtain 7.6 mg tipifarnib Form I; 76% yield.

Example 19

Placed 10 mg tipifarnib of Preparation Example 1 in 0.2 mL ethanol to obtain a solution, added 1.8 mL water, stirred for 30 minutes for crystallization and precipitation, vacuum filtrated, and then vacuum dried at room temperature for 10 hours to obtain 6.5 mg tipifarnib Form I; 65% yield.

Example 20

Placed 40 mg tipifarnib of Preparation Example 1 in 1.0 mL trifluoroethanol to obtain a solution, added 1.8 mL water, stirred for 30 minutes for crystallization and precipitation, vacuum filtrated, and then vacuum dried at room temperature for 10 hours to obtain 26 mg tipifarnib Form I; 65% yield.

Example 21

Form I can also be obtained by replacing the solvent in Example 20 with the following table.

| Experiment Number | Co-solvent | Anti-solvent |
|---|---|---|
| Experiment 1 | Trifluoroethanol | Isopropyl ether |
| Experiment 2 | Isopropanol | n-Heptane |
| Experiment 3 | n-Propanol | Water |
| Experiment 4 | Ethyl acetate | n-Heptane |
| Experiment 5 | Nitromethane | Isopropyl ether |

Example 22

Took 15 mg tipifarnib of Preparation Example 1, added 0.3 mL ethyl acetate to obtain a suspension, stirred at room temperature for 15 minutes for crystallization and precipitation, vacuum filtrated, and then vacuum dried at room temperature for 48 hours to obtain 12 mg tipifarnib Form I; 80% yield.

Example 23

Took 15 mg amorphous tipifarnib of Example 1, added 0.75 mL acetonitrile to obtain a suspension, stirred at room temperature for 15 minutes for crystallization and precipitation, vacuum filtrated, and then vacuum dried at room temperature for 24 hours to obtain 12.3 mg tipifarnib Form I; 82% yield.

Example 24

Took 15 mg amorphous tipifarnib of Example 1, added 0.15 mL ethanol to obtain a suspension, stirred at room temperature for 20 minutes for crystallization and precipitation, vacuum filtrated, and then vacuum dried at room temperature for 24 hours to obtain 10.5 mg tipifarnib Form I; 70% yield.

Example 25

Form I can also be obtained by replacing the solvent in Example 24 with the following table.

| Experiment Number | Solvent |
|---|---|
| Experiment 1 | Methanol |
| Experiment 2 | Isopropanol |
| Experiment 3 | Acetone |
| Experiment 4 | Butanone |
| Experiment 5 | Ethyl acetate |
| Experiment 6 | Isopropyl acetate |
| Experiment 7 | Isopropyl ether |
| Experiment 8 | methyl tert-butyl ether |
| Experiment 9 | n-Heptane |
| Experiment 10 | Methylcyclohexane |
| Experiment 11 | Tetrahydrofuran |

XRPD patterns, DSC thermograms, TGA thermograms (not shown) of the samples prepared in Examples 3 to 25 are the same as or similar to that of the sample prepared in Example 2, indicating the crystalline forms obtained in Examples 3 to 25 are the same as that of Example 2.

Example 26

Took 12 mg tipifarnib of Preparation Example 1, added 0.4 mL methanol to obtain a clear solution, volatilized at 10° C. to dryness to obtain 10 mg tipifarnib Form II; 80% yield.

Figure 6:
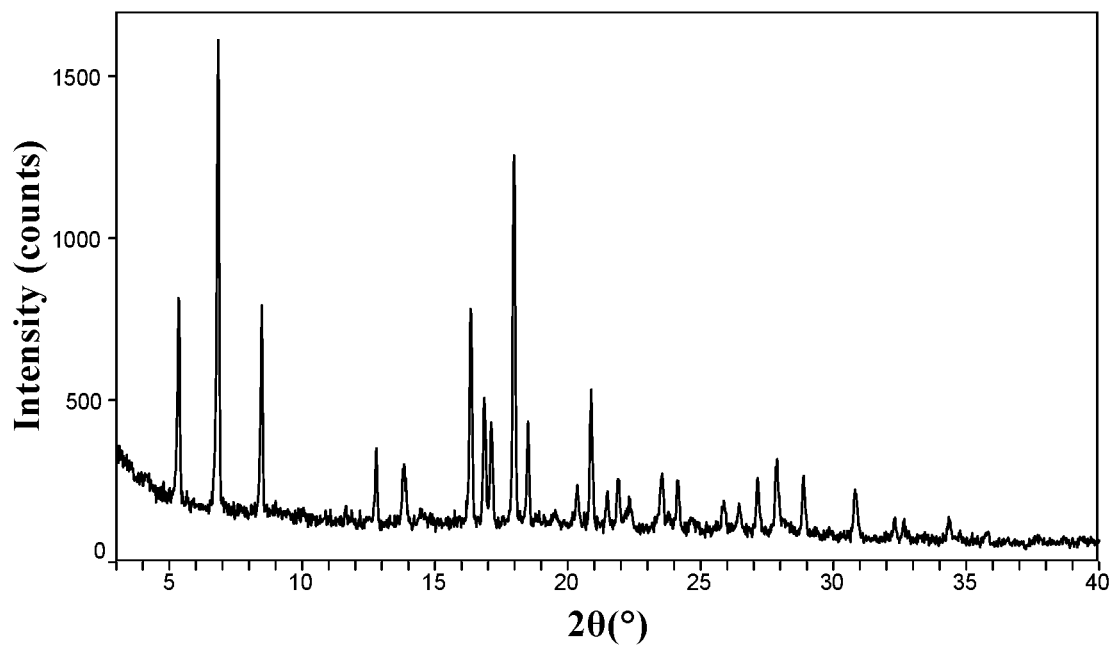
FIG. 6 is the XPRD pattern of tipifarnib Form II of the present invention.
Figure 7:
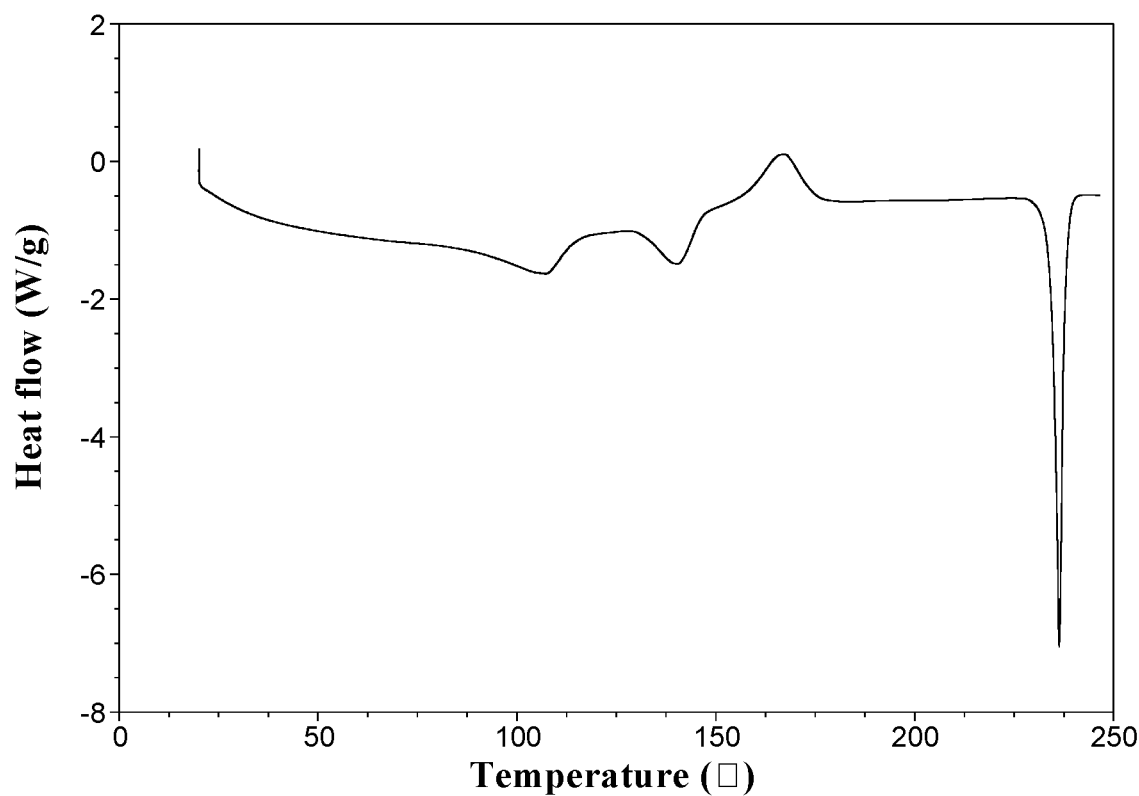
FIG. 7 is the DSC thermogram of tipifarnib Form II of the present invention.
Figure 8:
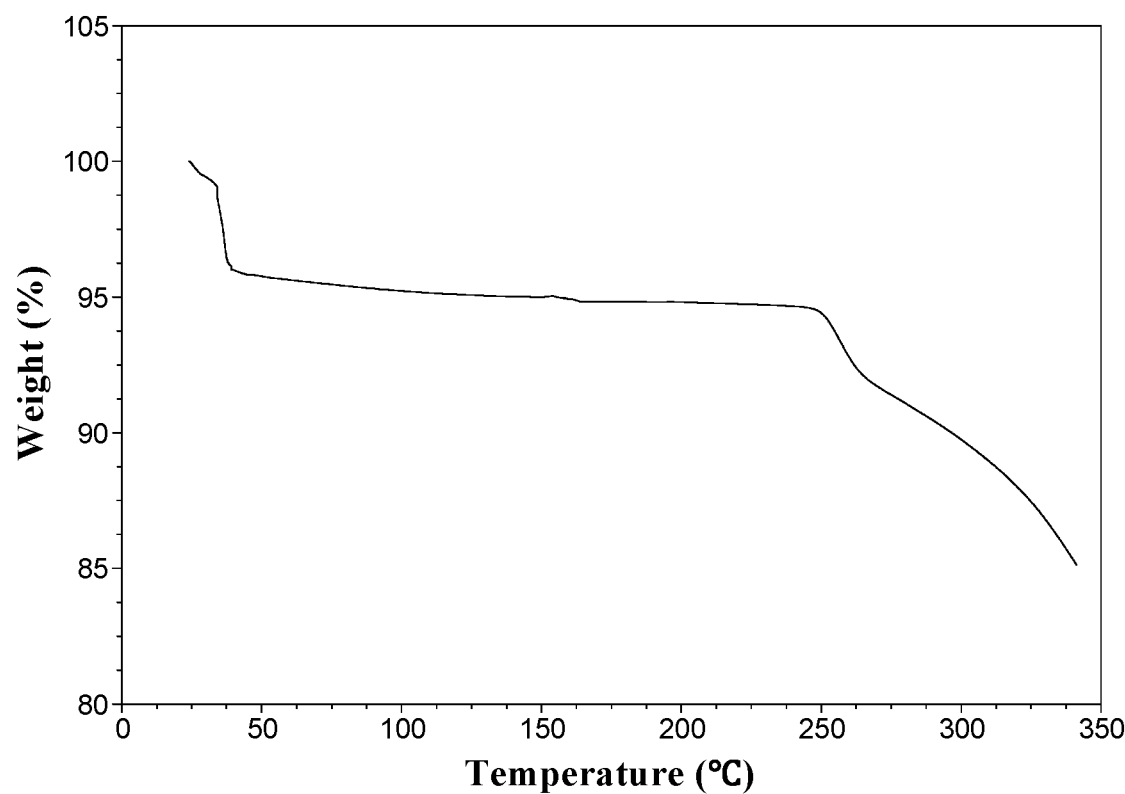
FIG. 8 is the TGA thermogram of tipifarnib Form II of the present invention.

Its XRPD pattern is shown in FIG. 6.
Its DSC thermogram is shown in FIG. 7.
Its TGA thermogram is shown in FIG. 8.

Example 27

Took 10 mg tipifarnib of Preparation Example 1, added 1.0 mL methanol to obtain a clear solution, volatilized at 30° C. to dryness to obtain 24 mg tipifarnib Form II; 77% yield.

Example 28

Took 50 mg tipifarnib of Preparation Example 1, added 1.0 mL trifluoroethanol to obtain a clear solution, volatilized at 40° C. to dryness to obtain 38 mg tipifarnib Form II; 73% yield.

Example 29

Form II can also be obtained by replacing the solvent in Example 28 with the following table.

| Experiment Number | Solvent 1 | Solvent 2 |
|---|---|---|
| Experiment 1 | Ethanol | — |
| Experiment 2 | Ethanol | Methanol |
| Experiment 3 | Ethanol | Trifluoroethanol |
| Experiment 4 | Methanol | Trifluoroethanol |

Example 30

Took 15 mg amorphous tipifarnib of Example 1, added 0.6 mL water to obtain a suspension, stirred at 25° C. for 15 minutes for crystallization and precipitation, vacuum filtrated, and then vacuum dried at 10° C. for 24 hours to obtain 14.1 mg tipifarnib Form II; 91% yield.

Example 31

Took 15.75 mg amorphous tipifarnib of Example 1, added a water-dimethyl sulfoxide solution (containing 85% water) 0.45 mL to obtain a suspension, stirred at 4° C. for 10 minutes for crystallization and precipitation, vacuum filtrated, and then vacuum dried at 30° C. for 10 hours to obtain 13.5 mg tipifarnib Form II; 83% yield.

Example 32

Took 10 mg amorphous tipifarnib of Example 1, added a water-ethanol solution (containing 50% water) 0.1 mL to obtain a suspension, stirred at 10° C. for 20 minutes for crystallization and precipitation, vacuum filtrated, and then vacuum dried at 25° C. for 20 hours to obtain 8.0 mg tipifarnib Form II; 77% yield.

Example 33

Form II can also be obtained by replacing the solvent in Example 32 with the following table.

| Experiment Number | Solvent 1 | Solvent 2 |
|---|---|---|
| Experiment 1 | Water | Methanol |
| Experiment 2 | Water | Isopropanol |
| Experiment 3 | Water | n-Propanol |
| Experiment 4 | Water | Acetone |
| Experiment 5 | Water | Tetrahydrofuran |
| Experiment 6 | Water | 1,4-dioxane |
| Experiment 7 | Water | Acetonitrile |

Example 34

Took 15 mg amorphous tipifarnib of Example 1, placed in a humidity dessicator with relative humidity of 97% for 1 day to obtain 14 mg tipifarnib Form II; 90% yield.

XRPD patterns, DSC thermograms, TGA thermograms (not shown) of the samples prepared in Examples 27 to 34 are the same as or similar to that of the sample prepared in Example 26, indicating the crystalline forms obtained in Examples 27 to 34 are the same as that of Example 26.

Example 35

Took 50 mg tipifarnib of Preparation Example 1, added a water-acetone solution (containing 50% water) 2.0 mL at 60° C. to obtain a clear solution, stirred at −10° C. for 1 hour for crystallization and precipitation, vacuum filtrated, and then vacuum dried at room temperature for 10 hours to obtain 43 mg tipifarnib Form III; 82% yield.

Figure 9:
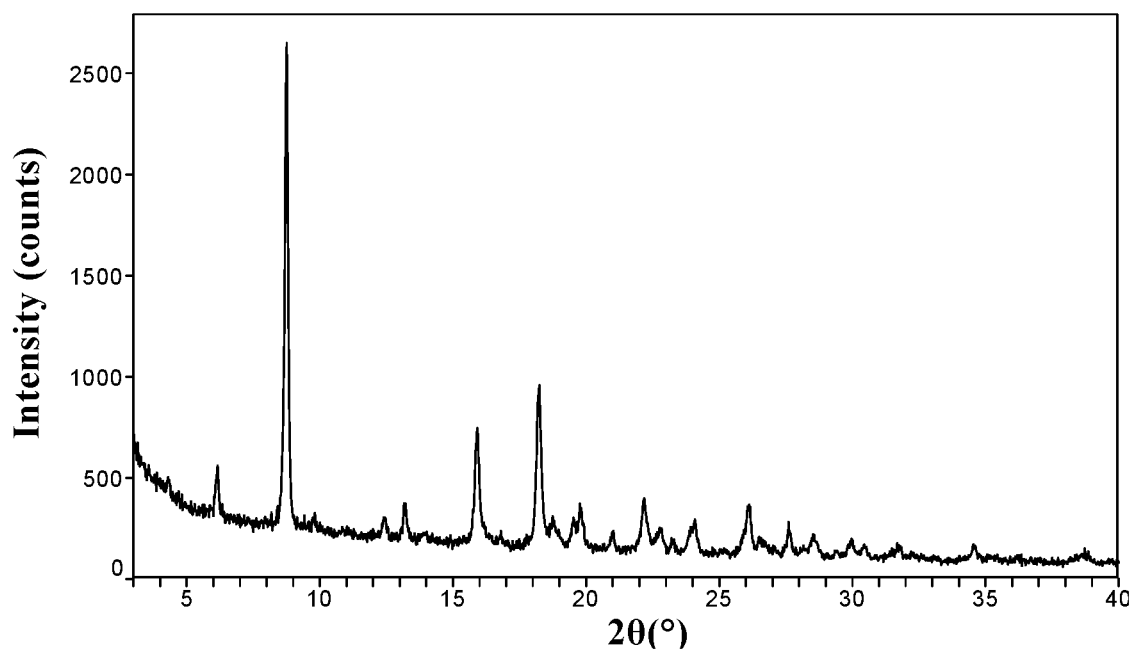
FIG. 9 is the XPRD pattern of tipifarnib Form III of the present invention.
Figure 10:
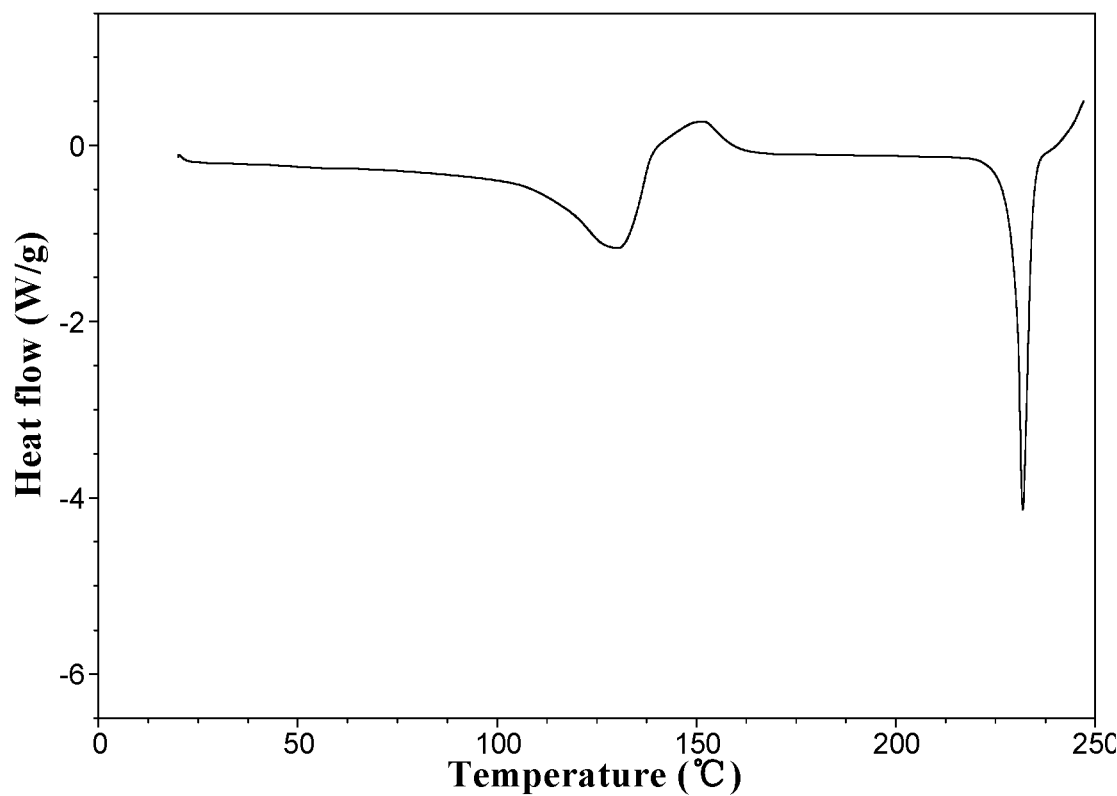
FIG. 10 is the DSC thermogram of tipifarnib Form III of the present invention.
Figure 11:
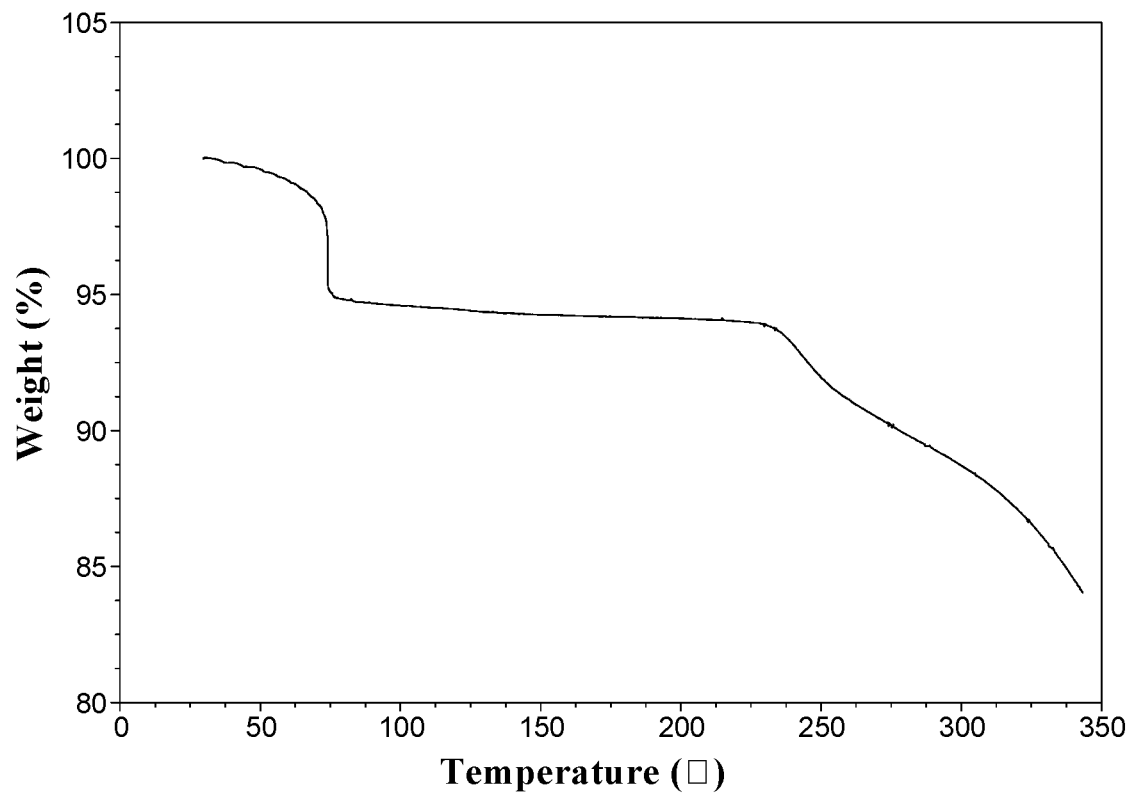
FIG. 11 is the TGA thermogram of tipifarnib Form III of the present invention.

Its XRPD pattern is shown in FIG. 9.
Its DSC thermogram is shown in FIG. 10.
Its TGA thermogram is shown in FIG. 11.

Example 36

Took 49 mg tipifarnib of Preparation Example 1, added a water-acetonitrile solution (containing 30% water) 3.5 mL at 70° C. to obtain a clear solution, stirred at 0° C. for 24 hours for crystallization and precipitation, vacuum filtrated, and then vacuum dried at room temperature for 24 hours to obtain 45 mg tipifarnib Form III; 87% yield.

Example 37

Placed 10 mg tipifarnib of Preparation Example 1 in 1.0 mL acetonitrile to obtain a solution, added 15.0 mL water, stirred at room temperature for 24 hours for crystallization and precipitation, vacuum filtrated, and then vacuum dried at 10° C. for 24 hours to obtain 8.0 mg tipifarnib Form III; 76% yield.

Example 38

Placed 10 mg tipifarnib of Preparation Example 1 in 0.4 mL 1,4-dioxane to obtain a clear solution, added 10.0 mL n-heptane, stirred at room temperature for 1 hour for crystallization and precipitation, vacuum filtrated, and then vacuum dried at 40° C. for 10 hours to obtain 8.5 mg tipifarnib Form III; 81% yield.

Example 39

Placed 10 mg tipifarnib of Preparation Example 1 in 5.0 mL isopropyl acetate to obtain a clear solution, added 15.0 mL n-heptane drop-wisely, stirred at room temperature for 2 hours for crystallization and precipitation, vacuum filtrated, and then vacuum dried at 30° C. for 12 hours to obtain 7.3 mg tipifarnib Form III; 69% yield.

Example 40

Form III can also be obtained by replacing the solvent in Example 39 with the following table.

| Experiment Number | Co-solvent | Anti-solvent |
|---|---|---|
| Experiment 1 | 1,4-dioxane | Water |
| Experiment 2 | Butanone | n-Heptane |

Example 41

Took 5 mg tipifarnib of Preparation Example 1, added a water-butanone solution (containing 1% water) 1.0 mL to obtain a clear solution, volatilized at 30° C. to dryness to obtain 4 mg tipifarnib Form III; 76% yield.

Example 42

Took 10 mg tipifarnib of Preparation Example 1, added a water-nitromethane solution (containing 2% water) 2.0 mL to obtain a clear solution, volatilized at 20° C. to dryness to obtain 7.6 mg tipifarnib Form III; 72% yield.

Example 43

Took 8 mg tipifarnib of Preparation Example 1, added a water-acetonitrile solution (containing 10% water) 1.0 mL to obtain a clear solution, volatilized at 10° C. to dryness to obtain 5.6 mg tipifarnib Form III; 66% yield.

Example 44

Form III can also be obtained by replacing the solvent in Example 43 with the following table.

| Experiment Number | Solvent 1 | Solvent 2 |
|---|---|---|
| Experiment 1 | Tetrahydrofuran | Water |
| Experiment 2 | 1,4-Dioxane | Water |

XRPD patterns, DSC thermograms, TGA thermograms (not shown) of the samples prepared in Examples 36 to 44 are the same as or similar to that of the sample prepared in Example 35, indicating the crystalline forms obtained in Examples 36 to 44 are the same as that of Example 35.

Example 45

Figure 12:
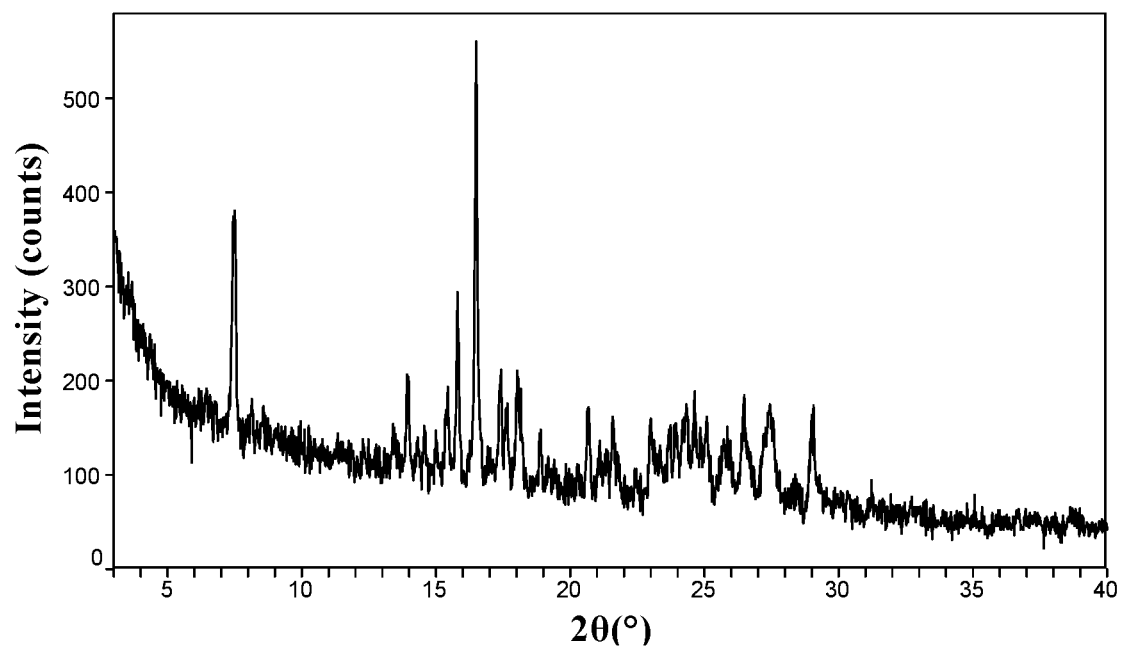
FIG. 12 is the XPRD pattern of tipifarnib Form IV of the present invention.
Figure 13:
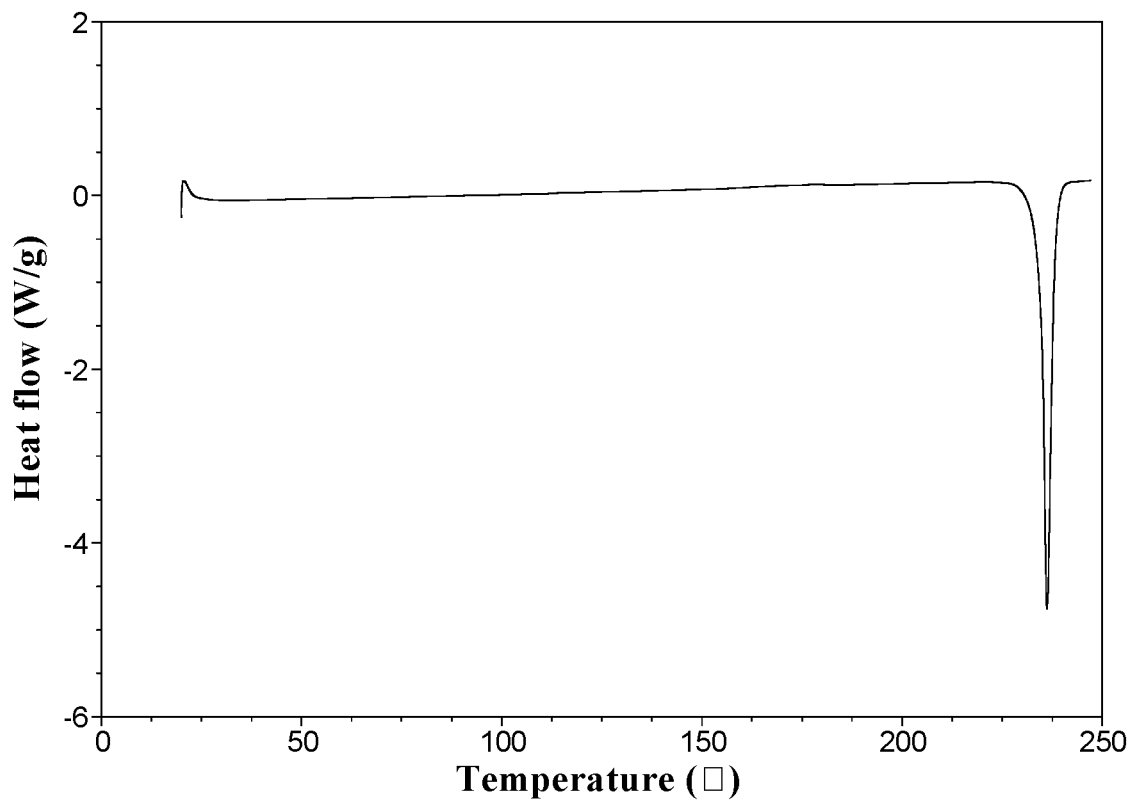
FIG. 13 is the DSC thermogram of tipifarnib Form IV of the present invention.
Figure 14:
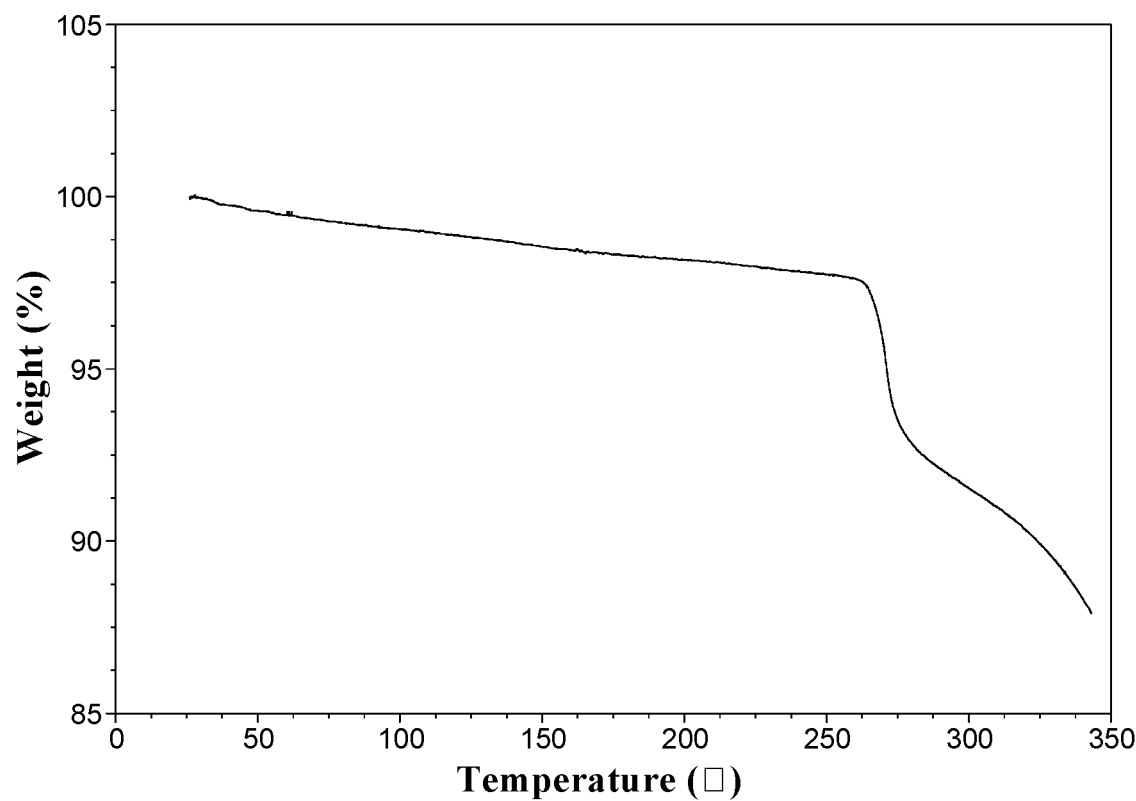
FIG. 14 is the TGA thermogram of tipifarnib Form IV of the present invention.

Took 10 mg tipifarnib of Preparation Example 1, added 1.0 mL ethanol to obtain a clear solution, volatilized at 40° C. to dryness to obtain 9.0 mg tipifarnib Form IV; 90% yield.
Its XRPD pattern is shown in FIG. 12.
Its DSC thermogram is shown in FIG. 13.
Its TGA thermogram is shown in FIG. 14.

Example 46

Took 10 mg tipifarnib of Preparation Example 1, added 0.4 mL chloroform to obtain a clear solution, volatilized at 50° C. to dryness to obtain 8.5 mg tipifarnib Form IV; 85% yield.

Example 47

Figure 15:
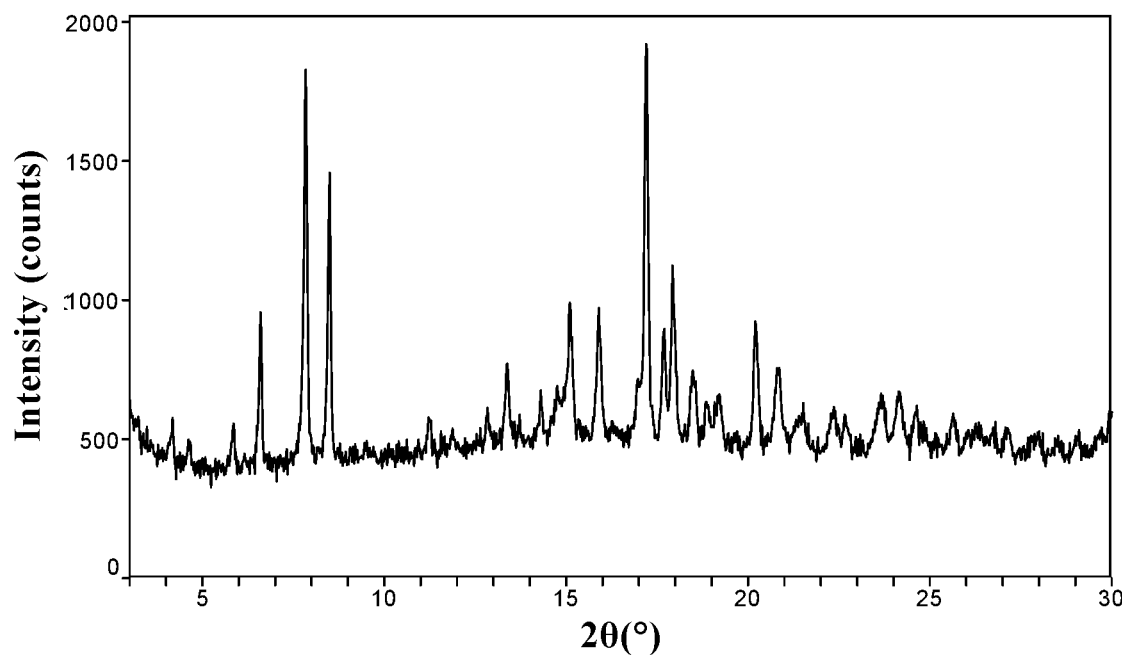
FIG. 15 is the XPRD pattern of tipifarnib Form V of the present invention.

Took 10 mg tipifarnib Form II of Example 26, heated to 120° C. at the rate of 30° C./min to obtain tipifarnib Form V.
Its XRPD pattern is shown in FIG. 15.

Example 48

Phase and chemical stability experiments: took 20 mg tipifarnib Form I, 20 mg Form II, 20 mg Form III and 20 mg Form IV of the present invention, placed at 60° C. dry condition and 40° C./75% RH condition respectively, and then analyzed by XRD at the corresponding time.

|  |  | 10 days test results | |
|---|---|---|---|
| Form | Condition | Form | Purity (%) |
| Form I | 60° C./drying | Tipifarnib Form I | 99.72 |
|  | 40° C./75% RH | Tipifarnib Form I | 99.61 |
| Form II | 60° C./drying | Tipifarnib Form II | 99.84 |
|  | 40° C./75% RH | Tipifarnib Form II | 99.86 |
| Form III | 60° C./drying | Tipifarnib Form III | 99.80 |
|  | 40° C./75% RH | Tipifarnib Form III | 99.80 |
| Form IV | 60° C./drying | Tipifarnib Form IV | 99.85 |
|  | 40° C./75% RH | Tipifarnib Form IV | 99.73 |

Tipifarnib Form I, Form II, Form III and Form IV of the present invention still remained their original forms and their purity essentially did not decrease after having been placed for 10 days at 60° C. drying condition and 40° C./75% RH condition, respectively. These results show that tipifarnib Form I, Form II, Form III and Form IV prepared by the present invention have good phase and chemical stability.

Example 49

Preparation of Tablet Core:
Mixed well 100 g tipifarnib Form I or Form II or Form III or Form IV (active ingredient basis) of the present invention, 570 g lactose and 200 g starch and then wetted with a solution of 5 g sodium dodecyl sulfate and 10 g polyvinylpyrrolidone in about 200 mL water. The wetted powder mixture was sifted, dried and then sifted again, then 100 g microcrystalline cellulose and 15 g hydrogenated vegetable oil were added. Mixed well the whole thing and compressed into tablets, resulting 10000 tablets, each comprising 10 mg active ingredient.
Coating:
To a solution of 10 g methylcellulose in 75 ml denatured ethanol added a solution of 5 g ethylcellulose in 150 ml dichloromethane, followed by addition of 75 ml dichloromethane and 2.5 ml 1,2,3-propanetriol. Melted 10 g polyethylene glycol and dissolved it in 75 ml dichloromethane. The latter solution was added to the former solution and then added 2.5 g magnesium octadecanoate, 5 g polyvinylpyrrolidone and 30 ml concentrated colour suspension and the whole thing was homogenated. The resulted mixture was used in a coating apparatus to coat the tablet cores.

Example 50

Dissolved 1.8 g methyl 4-hydroxybenzoate and 0.2 g propyl 4-hydroxybenzoate in about 0.5 ml boiling water for injection. After cooling the solution to about 50° C., while stirring added 4 g lactic acid, 0.05 g propylene glycol and 4 g tipifarnib Form I or Form II or Form III or Form IV (active ingredient basis) of the present invention. The above solution was cooled to room temperature and q.s. with water for injection to 1 L. This resulted a solution containing 4 mg/mL of tipifarnib Form I or Form II or Form III or Form IV (active ingredient basis). The solution was sterilized by filtration and filled in sterile containers.

Comparative Example 1

Slurry experiment in water: took 20 mg tipifarnib Form A of Preparation Example 1, 20 mg tipifarnib Form I, 20 mg Form II, 20 mg Form III and 20 mg Form IV of the present invention, stirred in water respectively at room temperature for 3 days, and then analyzed by XRD.

| Starting form | Test results |
| --- | --- |
| Tipifarnib Form A | Tipifarnib Form I |
| Tipifarnib Form I | Tipifarnib Form I |
| Tipifarnib Form II | Tipifarnib Form II |
| Tipifarnib Form III | Tipifarnib Form III |
| Tipifarnib Form IV | Tipifarnib Form IV |

The results show that tipifarnib Form A transformed to tipifanib Form I after stirring in water at room temperature for 3 days, while tipifarnib Form I, Form II, Form III and Form IV of the present invention remain unchanged. It shows that tipifarnib Form I, Form II, Form III and Form IV of the present invention is more stable in water than the prior art.

All patents, patent application publications, patent applications and non-patent publications cited in this specification are incorporated into this application by reference in their entireties.

The described above are only specific embodiments for illustrating the present invention, but without limiting it to that. Any changes or alternations, without creative work, made by those skilled in the art within the technical scope disclosed by the present invention, should fall within the scope of the present invention. Therefore, the scope of protection of the present invention shall be subject to the scope of protection defined in the claims.

What is claimed is:

1. A method of treating solid tumors and blood cancers associated with a RAS mutation or over expression in a patient, comprising administering to the patient, a therapeutically effective amount of tipifarnib Form I, having the chemical structure:

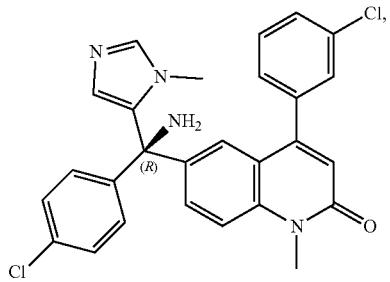

wherein, measured using Cu-Kα radiation, the X-ray powder diffraction pattern of the tipifarnib Form I, expressed as 2θ angles, has the following characteristic peaks: 8.4°±0.2°, 11.9°±0.2°, 16.4°±0.2°, 17.0°±0.2°, 18.5°±0.2° and 21.7°±0.2°;

wherein the solid tumors and blood cancers are selected from the group consisting of lung cancer, pancreatic cancer, colon cancer, thyroid follicular cancer, myelodysplastic syndrome, interstitial cell tumor, melanoma, teratoma, neuroblastoma, glioma, epidermal cancer, salivary gland cancer, skin benign tumor, breast cancer, kidney cancer, bone cancer, ovarian cancer, bladder cancer, liver cancer, multiple neurofibromatosis, hematologic lymphoma, myeloid leukemia, and chronic granulocytic leukemia.

2. The method of claim 1, wherein the epidermal cancer is head and neck squamous cell carcinoma.

3. The method of claim 1, wherein the hematologic lymphoma is peripheral T cell lymphoma.

4. The method of claim 1, wherein the tipifarnib Form I is administered as two, three, four or more sub-doses throughout the day.

5. The method of claim 4, wherein the sub-dose is formulated as a unit dosage form containing 0.01-500 mg of tipifarnib Form I.

6. The method of claim 4, wherein the sub-dose is formulated as a unit dosage form containing 0.01-200 mg of tipifarnib Form I.

7. A method of treating solid tumors and blood cancers associated with a RAS mutation or over expression in a patient comprising administering to the patient, a therapeutically effective amount of tipifarnib Form II, having the chemical structure:

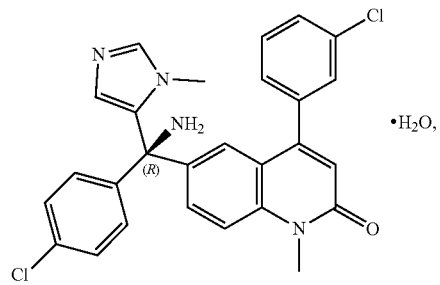

wherein, measured using Cu-Kα radiation, the X-ray powder diffraction pattern of the tipifarnib Form II, expressed as 2θ angles, has the following characteristic peaks: 5.3°±0.2°, 6.8°±0.2°, 8.5°±0.2°, 16.3°±0.2°, 18.0°±0.2° and 20.9°±0.2°;

wherein the solid tumors and blood cancers are selected from the group consisting of lung cancer, pancreatic cancer, colon cancer, thyroid follicular cancer, myelodysplastic syndrome, interstitial cell tumor, melanoma, teratoma, neuroblastoma, glioma, epidermal cancer, salivary gland cancer, skin benign tumor, breast cancer, kidney cancer, bone cancer, ovarian cancer, bladder cancer, liver cancer, multiple neurofibromatosis, hematologic lymphoma, myeloid leukemia, and chronic granulocytic leukemia.

8. The method of claim 7, wherein the epidermal cancer is head and neck squamous cell carcinoma.

9. The method of claim 7, wherein the hematologic lymphoma is peripheral T cell lymphoma.

10. The method of claim 7, wherein the tipifarnib Form II is administered as two, three, four or more sub-doses throughout the day.

11. The method of claim 10, wherein the sub-dose is formulated as a unit dosage form containing 0.01-500 mg of tipifarnib Form II.

12. The method of claim 10, wherein the sub-dose is formulated as a unit dosage form containing 0.01-200 mg of tipifarnib Form II.

13. A method of treating solid tumors and blood cancers associated with a RAS mutation or over expression in a patient comprising administering to the patient, a therapeutically effective amount of tipifarnib Form III, having the chemical structure:

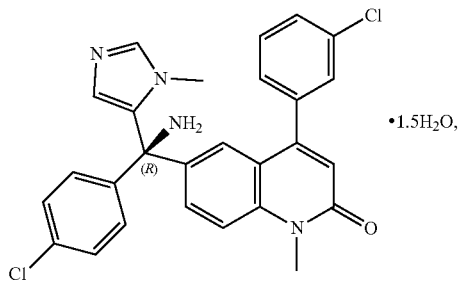

•1.5H$_2$O, wherein, measured using Cu-Kα radiation, the X-ray powder diffraction pattern of the tipifarnib Form III, expressed as 2θ angles, has the following characteristic peaks: 6.2°±0.2°, 8.8°±0.2°, 15.9°±0.2° and 18.2°±0.2°;

wherein the solid tumors and blood cancers are selected from the group consisting of lung cancer, pancreatic cancer, colon cancer, thyroid follicular cancer, myelodysplastic syndrome, interstitial cell tumor, melanoma, teratoma, neuroblastoma, glioma, epidermal cancer, salivary gland cancer, skin benign tumor, breast cancer, kidney cancer, bone cancer, ovarian cancer, bladder cancer, liver cancer, multiple neurofibromatosis, hematologic lymphoma, myeloid leukemia, and chronic granulocytic leukemia.

14. The method of claim 13, wherein the epidermal cancer is head and neck squamous cell carcinoma.

15. The method of claim 13, wherein the hematologic lymphoma is peripheral T cell lymphoma.

16. The method of claim 13, wherein the tipifarnib Form III is administered as two, three, four or more sub-doses throughout the day.

17. The method of claim 16, wherein the sub-dose is formulated as a unit dosage form containing 0.01-500 mg of tipifarnib Form III.

18. The method of claim 16, wherein the sub-dose is formulated as a unit dosage form containing 0.01-200 mg of tipifarnib Form III.

19. A method of treating solid tumors and blood cancers associated with a RAS mutation or over expression in a patient comprising administering to the patient, a therapeutically effective amount of tipifarnib Form IV, having the chemical structure:

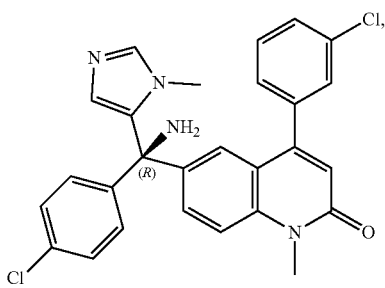

wherein, measured using Cu-Kα radiation, the X-ray powder diffraction pattern of the tipifarnib Form IV, expressed as 2θ angles, has the following characteristic peaks: 7.5°±0.2°, 13.9°±0.2°, 15.8°±0.2°, 16.5°±0.2°, 17.4°±0.2° and 18.1°±0.2°;

wherein the solid tumors and blood cancers are selected from the group consisting of lung cancer, pancreatic cancer, colon cancer, thyroid follicular cancer, myelodysplastic syndrome, interstitial cell tumor, melanoma, teratoma, neuroblastoma, glioma, epidermal cancer, salivary gland cancer, skin benign tumor, breast cancer, kidney cancer, bone cancer, ovarian cancer, bladder cancer, liver cancer, multiple neurofibromatosis, hematologic lymphoma, myeloid leukemia, and chronic granulocytic leukemia.

20. The method of claim 19, wherein the epidermal cancer is head and neck squamous cell carcinoma.

21. The method of claim 19, wherein the hematologic lymphoma is peripheral T cell lymphoma.

22. The method of claim 19, wherein the tipifarnib Form IV is administered as two, three, four or more sub-doses throughout the day.

23. The method of claim 22, wherein the sub-dose is formulated as a unit dosage form containing 0.01-500 mg of tipifarnib Form IV.

24. The method of claim 22, wherein the sub-dose is formulated as a unit dosage form containing 0.01-200 mg of tipifarnib Form IV.

* * * * *